United States Patent
Gaines et al.

(10) Patent No.: US 9,020,419 B2
(45) Date of Patent: Apr. 28, 2015

(54) WIRELESS RELAY MODULE FOR REMOTE MONITORING SYSTEMS HAVING POWER AND MEDICAL DEVICE PROXIMITY MONITORING FUNCTIONALITY

(75) Inventors: Robert B Gaines, Lake Saint Louis, MO (US); John Holste, Hamburg, IL (US); Kenneth M Breitweiser, Brighton, IL (US); Joel D Wiesner, St. Peters, MO (US)

(73) Assignee: Covidien, LP, Mansfield, MA (US)

( * ) Notice: Subject to any disclaimer, the term of this patent is extended or adjusted under 35 U.S.C. 154(b) by 211 days.

(21) Appl. No.: 13/353,565

(22) Filed: Jan. 19, 2012

(65) Prior Publication Data
US 2012/0182143 A1    Jul. 19, 2012

Related U.S. Application Data

(63) Continuation-in-part of application No. 13/334,463, filed on Dec. 22, 2011, and a continuation-in-part of application No. 13/006,769, filed on Jan. 14, 2011, now Pat. No. 8,818,260.

(51) Int. Cl.
*H04B 7/15* (2006.01)
*G08B 21/04* (2006.01)
(Continued)

(52) U.S. Cl.
CPC ......... *G08B 21/0453* (2013.01); *A61B 5/0022* (2013.01); *A61B 5/02* (2013.01); *A61B 2560/0271* (2013.01); *G08B 21/0277* (2013.01)

(58) Field of Classification Search
CPC ..... H04W 88/04; H04W 84/18; H04W 40/02; H04W 76/007; H04W 24/00; G06F 19/3418; H04L 45/70; H04L 67/12; A61B 5/0022; A61B 5/746; A61B 2560/0271; G08B 21/0277; G08B 21/0453
USPC ........... 455/11.1, 414.1, 410, 7, 16, 500, 507, 455/51, 566; 705/2; 709/217–219; 370/315, 370/252
See application file for complete search history.

(56) References Cited

U.S. PATENT DOCUMENTS

| 5,451,839 A | 9/1995 | Rappaport et al. |
| 5,936,539 A | 8/1999 | Fuchs |

(Continued)

FOREIGN PATENT DOCUMENTS

| CA | 2 644 695 | 1/2004 |
| CA | 2 648 885 | 11/2007 |

(Continued)

OTHER PUBLICATIONS

Response filed Aug. 14, 2013; to Office Action dated May 15, 2013; for U.S. Appl. No. 13/006,784; 13 pages.

(Continued)

*Primary Examiner* — Sujatha Sharma
(74) *Attorney, Agent, or Firm* — Lisa E. Winsor, Esq.

(57) ABSTRACT

Wireless relay modules for networked communications between a medical device and a remote monitoring device via wireless relay networks and/or internet-accessible wireless communications networks. The wireless relay module includes a receiver, a first transmitter coupled to the wireless relay network, a second transmitter coupled to the internet-accessible wireless communication network, a controller and a display. The controller is coupled to the first and second transmitters, and controls the wireless relay module to select one of the transmitters for transmitting medical device data over one of the two respective networks. The controller generates an alarm signal and stores storing wirelessly-received medical device data in a memory of the wireless relay module upon detecting a changed characteristic for a power source of the wireless relay module. The controller also generates an alarm upon detecting a change in a characteristic of a signal transmitted by the medical device.

45 Claims, 11 Drawing Sheets

(51) Int. Cl.
*A61B 5/00* (2006.01)
*G08B 21/02* (2006.01)
*A61B 5/02* (2006.01)

(56) References Cited

U.S. PATENT DOCUMENTS

| | | | |
|---|---|---|---|
| 6,221,012 B1 | 4/2001 | Maschke et al. | |
| 6,377,162 B1 | 4/2002 | Delestienne et al. | |
| 6,377,806 B1 | 4/2002 | Tokuyoshi | |
| 6,442,433 B1 | 8/2002 | Linberg | |
| 6,519,569 B1 | 2/2003 | White et al. | |
| 6,578,002 B1 | 6/2003 | Derzay et al. | |
| 6,790,198 B1 | 9/2004 | White et al. | |
| 6,831,557 B1 | 12/2004 | Hess | |
| 6,839,753 B2 | 1/2005 | Biondi et al. | |
| 7,028,182 B1* | 4/2006 | Killcommons | 713/161 |
| 7,050,984 B1 | 5/2006 | Kerpelman et al. | |
| 7,082,460 B2 | 7/2006 | Hansen et al. | |
| 7,178,149 B2 | 2/2007 | Hansen | |
| 7,185,014 B1 | 2/2007 | Hansen | |
| 7,236,936 B2 | 6/2007 | White et al. | |
| 7,294,105 B1 | 11/2007 | Islam | |
| 7,316,648 B2 | 1/2008 | Kelly | |
| 7,349,947 B1* | 3/2008 | Slage et al. | 709/217 |
| 7,508,787 B2 | 3/2009 | Doshi et al. | |
| 7,512,889 B2 | 3/2009 | Newell et al. | |
| 7,529,561 B2 | 5/2009 | Heinonen et al. | |
| 7,539,532 B2 | 5/2009 | Tran | |
| 7,539,533 B2 | 5/2009 | Tran | |
| 7,558,622 B2 | 7/2009 | Tran | |
| 7,605,714 B2 | 10/2009 | Thompson et al. | |
| 7,613,169 B2 | 11/2009 | Vaittinen et al. | |
| 7,645,258 B2 | 1/2010 | White et al. | |
| 7,707,047 B2 | 4/2010 | Hasan et al. | |
| 7,733,224 B2 | 6/2010 | Tran | |
| 7,749,164 B2 | 7/2010 | Davis | |
| 7,752,058 B2* | 7/2010 | Sasaki et al. | 705/3 |
| 7,827,040 B2 | 11/2010 | Brown | |
| 7,873,772 B2 | 1/2011 | Waldhoff et al. | |
| 7,937,370 B2 | 5/2011 | Hansen | |
| 7,942,844 B2 | 5/2011 | Moberg et al. | |
| 7,949,404 B2 | 5/2011 | Hill | |
| 7,978,062 B2 | 7/2011 | LaLonde | |
| 8,002,701 B2 | 8/2011 | John et al. | |
| RE42,934 E | 11/2011 | Thompson | |
| 8,073,008 B2* | 12/2011 | Mehta et al. | 370/468 |
| 8,095,381 B2 | 1/2012 | Simmons et al. | |
| 8,108,543 B2 | 1/2012 | Hansen | |
| 8,125,318 B2 | 2/2012 | Heimbrock et al. | |
| 8,126,728 B2 | 2/2012 | Dicks et al. | |
| 8,126,729 B2 | 2/2012 | Dicks et al. | |
| 8,126,730 B2 | 2/2012 | Dicks et al. | |
| 8,126,732 B2 | 2/2012 | Dicks et al. | |
| 8,126,733 B2 | 2/2012 | Dicks et al. | |
| 8,126,734 B2 | 2/2012 | Dicks et al. | |
| 8,126,735 B2 | 2/2012 | Dicks et al. | |
| 8,131,564 B2 | 3/2012 | Dicks et al. | |
| 8,131,565 B2 | 3/2012 | Dicks et al. | |
| 8,131,566 B2 | 3/2012 | Dicks et al. | |
| 8,140,356 B2 | 3/2012 | Dicks et al. | |
| 8,155,982 B2 | 4/2012 | Dicks et al. | |
| 8,200,195 B2 | 6/2012 | Le Saint et al. | |
| 8,214,549 B2 | 7/2012 | Dicks et al. | |
| 8,279,061 B2 | 10/2012 | Soliman | |
| 8,326,648 B2* | 12/2012 | Kenedy et al. | 705/2 |
| 8,373,556 B2 | 2/2013 | LaLonde et al. | |
| 8,395,498 B2 | 3/2013 | Gaskill et al. | |
| 8,428,722 B2 | 4/2013 | Verhoef et al. | |
| 8,515,547 B2 | 8/2013 | Mass et al. | |
| 8,587,427 B2 | 11/2013 | LaLonde et al. | |
| 8,694,600 B2 | 4/2014 | Gaines et al. | |
| 8,855,550 B2 | 10/2014 | Gaines et al. | |
| 2002/0178126 A1 | 11/2002 | Beck et al. | |
| 2002/0198473 A1 | 12/2002 | Kumar et al. | |
| 2004/0034284 A1 | 2/2004 | Aversano et al. | |
| 2004/0155772 A1 | 8/2004 | Medema et al. | |
| 2004/0204743 A1 | 10/2004 | McGrath et al. | |
| 2005/0010093 A1 | 1/2005 | Ford et al. | |
| 2005/0185398 A1 | 8/2005 | Scannell, Jr. | |
| 2005/0188853 A1 | 9/2005 | Scannell, Jr. | |
| 2005/0201300 A1 | 9/2005 | Bridgelall | |
| 2005/0206518 A1 | 9/2005 | Welch et al. | |
| 2005/0234308 A1 | 10/2005 | Naukkarinen | |
| 2005/0243988 A1 | 11/2005 | Barclay et al. | |
| 2005/0288571 A1 | 12/2005 | Perkins et al. | |
| 2006/0066449 A1 | 3/2006 | Johnson | |
| 2006/0121846 A1 | 6/2006 | Mazar et al. | |
| 2006/0154642 A1 | 7/2006 | Scannell, Jr. | |
| 2006/0224048 A1 | 10/2006 | Devaul et al. | |
| 2006/0226960 A1 | 10/2006 | Pisz et al. | |
| 2006/0238333 A1 | 10/2006 | Welch et al. | |
| 2006/0252999 A1 | 11/2006 | Devaul et al. | |
| 2007/0106126 A1 | 5/2007 | Mannheimer et al. | |
| 2007/0135866 A1 | 6/2007 | Baker et al. | |
| 2007/0156033 A1 | 7/2007 | Causey, III et al. | |
| 2007/0180140 A1 | 8/2007 | Welch et al. | |
| 2007/0186923 A1 | 8/2007 | Poutiatine et al. | |
| 2007/0216764 A1 | 9/2007 | Kwak | |
| 2007/0230197 A1 | 10/2007 | Scannell, Jr. | |
| 2007/0254593 A1* | 11/2007 | Jollota et al. | 455/67.11 |
| 2007/0255125 A1 | 11/2007 | Moberg et al. | |
| 2007/0255250 A1 | 11/2007 | Moberg et al. | |
| 2007/0257788 A1 | 11/2007 | Carlson et al. | |
| 2007/0258395 A1* | 11/2007 | Jollota et al. | 370/310 |
| 2007/0268726 A1 | 11/2007 | Scannell, Jr. | |
| 2007/0276270 A1 | 11/2007 | Tran | |
| 2008/0001735 A1 | 1/2008 | Tran | |
| 2008/0004904 A1 | 1/2008 | Tran | |
| 2008/0004907 A1* | 1/2008 | Bayne | 705/2 |
| 2008/0012761 A1 | 1/2008 | Derrick et al. | |
| 2008/0024294 A1 | 1/2008 | Mazar | |
| 2008/0071234 A1 | 3/2008 | Kelch et al. | |
| 2008/0088436 A1 | 4/2008 | Reeves et al. | |
| 2008/0097550 A1 | 4/2008 | Dicks et al. | |
| 2008/0097551 A1 | 4/2008 | Dicks et al. | |
| 2008/0097552 A1 | 4/2008 | Dicks et al. | |
| 2008/0097793 A1 | 4/2008 | Dicks et al. | |
| 2008/0097908 A1 | 4/2008 | Dicks et al. | |
| 2008/0097909 A1 | 4/2008 | Dicks et al. | |
| 2008/0097910 A1 | 4/2008 | Dicks et al. | |
| 2008/0097911 A1 | 4/2008 | Dicks et al. | |
| 2008/0097912 A1 | 4/2008 | Dicks et al. | |
| 2008/0097913 A1 | 4/2008 | Dicks et al. | |
| 2008/0097914 A1 | 4/2008 | Dicks et al. | |
| 2008/0097917 A1 | 4/2008 | Dicks et al. | |
| 2008/0103370 A1 | 5/2008 | Dicks et al. | |
| 2008/0108880 A1 | 5/2008 | Young et al. | |
| 2008/0136652 A1 | 6/2008 | Vaisnys et al. | |
| 2008/0139890 A1 | 6/2008 | Craine et al. | |
| 2008/0146277 A1 | 6/2008 | Anglin et al. | |
| 2008/0146890 A1 | 6/2008 | LeBoeuf et al. | |
| 2008/0183502 A1 | 7/2008 | Dicks et al. | |
| 2008/0224852 A1 | 9/2008 | Dicks et al. | |
| 2008/0228045 A1 | 9/2008 | Gao et al. | |
| 2008/0281168 A1 | 11/2008 | Gibson et al. | |
| 2008/0294019 A1 | 11/2008 | Tran | |
| 2008/0294020 A1 | 11/2008 | Sapounas | |
| 2009/0019061 A1 | 1/2009 | Scannell, Jr. | |
| 2009/0023391 A1 | 1/2009 | Falck | |
| 2009/0036750 A1 | 2/2009 | Weinstein et al. | |
| 2009/0058635 A1 | 3/2009 | LaLonde et al. | |
| 2009/0058636 A1 | 3/2009 | Gaskill et al. | |
| 2009/0062887 A1 | 3/2009 | Mass et al. | |
| 2009/0063187 A1 | 3/2009 | Johnson et al. | |
| 2009/0063193 A1 | 3/2009 | Barton et al. | |
| 2009/0069642 A1 | 3/2009 | Gao et al. | |
| 2009/0073694 A1 | 3/2009 | Scannell, Jr. | |
| 2009/0105549 A1 | 4/2009 | Smith et al. | |
| 2009/0115628 A1 | 5/2009 | Dicks et al. | |
| 2009/0128320 A1 | 5/2009 | Needham et al. | |
| 2009/0140851 A1 | 6/2009 | Graves et al. | |
| 2009/0149722 A1 | 6/2009 | Abolfathi et al. | |
| 2009/0184835 A1* | 7/2009 | Deaver et al. | 340/660 |
| 2009/0203329 A1 | 8/2009 | White et al. | |

(56) References Cited

U.S. PATENT DOCUMENTS

| | | |
|---|---|---|
| 2009/0234672 A1 | 9/2009 | Dicks et al. |
| 2009/0247114 A1 | 10/2009 | Sennett et al. |
| 2009/0252117 A1 | 10/2009 | Sherman et al. |
| 2009/0299788 A1 | 12/2009 | Huber et al. |
| 2009/0306747 A1 | 12/2009 | Fischer et al. |
| 2009/0326339 A1 | 12/2009 | Horvitz |
| 2010/0011000 A1 | 1/2010 | Chakara et al. |
| 2010/0027518 A1 | 2/2010 | Wang |
| 2010/0077115 A1 | 3/2010 | Rofougaran |
| 2010/0079276 A1 | 4/2010 | Collins et al. |
| 2010/0080200 A1 | 4/2010 | Stewart |
| 2010/0082371 A1 | 4/2010 | Kamp et al. |
| 2010/0085948 A1 | 4/2010 | Yu et al. |
| 2010/0094098 A1 | 4/2010 | Smith et al. |
| 2010/0117835 A1 | 5/2010 | Nanikashvili |
| 2010/0138235 A1 | 6/2010 | Marks et al. |
| 2010/0166170 A1 | 7/2010 | East |
| 2010/0198142 A1 | 8/2010 | Sloan et al. |
| 2010/0217723 A1 | 8/2010 | Sauerwein, Jr. et al. |
| 2010/0219250 A1 | 9/2010 | Wang |
| 2010/0222645 A1 | 9/2010 | Nadler et al. |
| 2010/0234695 A1 | 9/2010 | Morris |
| 2010/0260061 A1 | 10/2010 | Bojahra et al. |
| 2010/0279647 A1 | 11/2010 | Jacobs et al. |
| 2010/0292556 A1 | 11/2010 | Golden |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032818 A1* | 2/2011 | Yamaguchi et al. .......... 370/225 |
| 2011/0032822 A1 | 2/2011 | Soomro |
| 2011/0066555 A1 | 3/2011 | Dicks et al. |
| 2011/0078441 A1 | 3/2011 | Dicks et al. |
| 2011/0087756 A1 | 4/2011 | Biondi et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0148624 A1 | 6/2011 | Eaton et al. |
| 2011/0158430 A1 | 6/2011 | Dicks et al. |
| 2011/0161111 A1 | 6/2011 | Dicks et al. |
| 2011/0179405 A1 | 7/2011 | Dicks et al. |
| 2011/0255454 A1 | 10/2011 | Hauser et al. |
| 2011/0270045 A1 | 11/2011 | Lebel et al. |
| 2011/0273287 A1 | 11/2011 | LaLonde et al. |
| 2011/0280224 A1 | 11/2011 | Falck et al. |
| 2011/0282671 A1 | 11/2011 | Dicks et al. |
| 2011/0292862 A1 | 12/2011 | Shimizu |
| 2012/0004925 A1 | 1/2012 | Braverman et al. |
| 2012/0108917 A1 | 5/2012 | Libbus et al. |
| 2012/0182143 A1 | 7/2012 | Gaines et al. |
| 2012/0182894 A1 | 7/2012 | Gaines et al. |
| 2012/0182924 A1 | 7/2012 | Gaines et al. |
| 2012/0182927 A1 | 7/2012 | Wiesner et al. |
| 2012/0184207 A1* | 7/2012 | Gaines et al. ................ 455/11.1 |
| 2012/0184237 A1 | 7/2012 | Gaines et al. |
| 2012/0185268 A1* | 7/2012 | Wiesner et al. .................... 705/2 |
| 2012/0226768 A1* | 9/2012 | Gaines et al. ................ 709/217 |
| 2012/0226771 A1* | 9/2012 | Harrington et al. .......... 709/217 |
| 2012/0256751 A1 | 10/2012 | Nallabelli et al. |
| 2012/0293323 A1 | 11/2012 | Kaib et al. |
| 2013/0015966 A1 | 1/2013 | Soomro et al. |
| 2013/0021169 A1 | 1/2013 | Soomro et al. |
| 2013/0022022 A1 | 1/2013 | Schmitt |
| 2013/0066644 A1 | 3/2013 | Dicks et al. |
| 2013/0147622 A1 | 6/2013 | LaLonde et al. |
| 2013/0154851 A1 | 6/2013 | Gaskill et al. |
| 2013/0162426 A1 | 6/2013 | Wiesner et al. |
| 2013/0278414 A1 | 10/2013 | Sprigg et al. |
| 2013/0310896 A1 | 11/2013 | Mass |
| 2014/0009271 A1 | 1/2014 | Collins et al. |
| 2014/0062718 A1 | 3/2014 | LaLonde et al. |
| 2014/0142979 A1 | 5/2014 | Mitsunaga |
| 2014/0152466 A1 | 6/2014 | Wiesner et al. |

FOREIGN PATENT DOCUMENTS

| | | |
|---|---|---|
| CA | 2 644 635 | 8/2008 |
| CN | 101601040 A | 12/2009 |
| EP | 2227063 A1 | 9/2010 |
| JP | 2003109160 | 4/2003 |
| JP | 2006520657 | 9/2006 |
| JP | 2007531442 | 11/2007 |
| JP | 2008108170 | 5/2008 |
| JP | 2009-535715 A | 1/2009 |
| JP | 2010-524050 | 7/2010 |
| JP | 2010-524050 A | 7/2010 |
| JP | 2011-502369 A | 1/2011 |
| KR | 10-2008-0016458 A | 2/2008 |
| KR | 10-2009-0122968 A | 12/2009 |
| KR | 10-2010-0028318 A | 3/2010 |
| WO | WO 94/16617 | 8/1994 |
| WO | WO 98/14228 A1 | 4/1998 |
| WO | WO 03/048919 A1 | 6/2003 |
| WO | WO 2004/070994 A2 | 8/2004 |
| WO | WO 2004/070994 A3 | 8/2004 |
| WO | WO 2004/084720 A2 | 10/2004 |
| WO | WO 2005/057294 A1 | 6/2005 |
| WO | WO 2005/057834 A2 | 6/2005 |
| WO | WO 2005/098736 A2 | 10/2005 |
| WO | WO 2007/124091 A1 | 11/2007 |
| WO | WO 2007/127879 A2 | 11/2007 |
| WO | WO 2008/052034 A1 | 5/2008 |
| WO | WO 2008/097316 A1 | 8/2008 |
| WO | WO 2009/032134 A2 | 3/2009 |
| WO | WO 2009/0633030 A1 | 5/2009 |
| WO | WO 2010/085138 A2 | 7/2010 |

OTHER PUBLICATIONS

Atmel Corporation, "ZigBee Pro Stack and Software Development Kit," http://www.meshnetics.com/wsn-software/, Nov. 4, 2011.

Bacheldor, "Hospital Tries ZigBee to Track Patients," RFID Journal, Jul. 21, 2006.

BelAir Networks, "Capacity of Wireless Mesh Networks," white paper, 2006.

Bogia, "Enabling the future of u-Health-IEEE 11073 Personal Health Device Standards," slides, Sep. 16, 2009.

Bowman, "Newly Ratified ZigBee Health Care Profile Now Available for Public Download," http://www.fiercehealthcare.com/node/40708, Apr. 6, 2010.

Craig, "ZigBee Networks," http://medicaldesign.com/electrical-components/zigbee_networks/, Apr. 1, 2005.

Craig, "ZigBee: 'Wireless Control That Simply Works'," https://docs.zigbee.org/zigbee-docs/dcn/04-1427.pdf, prior to Jan. 2011.

Digi International Inc., "ConnectPort® X4 H," retrieved from the Internet: http://www.digi.com, 2008-2010.

Digi International Inc., "Demystifying 802.15.4 and ZigBee®," white paper, retrieved from the Internet: http://www.digi.com, 2008-2010.

Digi International Inc., "XBee® & XBee-PRO® ZB," retrieved from the Internet: http://www.digi.com, 2008-2010.

Digi International Inc., "XBee® & XBee-PRO® ZB ZigBee® PRO RF Modules," http://www.digi.com/products/wireless/zigbee-mesh/xbee-zb-module,jsp, Nov. 2, 2010.

Dvorak, "Remote Monitoring," http://medicaldesign.com/electrical-components/remote_monitoring/index.html, Apr. 1, 2005.

ENP Newswire, "Freescale products achieve ZigBee Health Care Certification," May 19, 2010.

Huang, "Medical electronics: from hospital and clinic to the home," http://www.eetimes.com/General/DisplayPrintViewContent?contentItemid=4211247, Dec. 8, 2010.

ICP DAS, "ZigBee Converter User's Manual," Sep. 22, 2008.

Le, "Designing a ZigBee-ready IEEE 802.15.4-compliant radio transceiver," http://rfdesign.com/mag/411rfdf4.pdf, Nov. 2004.

Norris et al., "Single-chip ZigBee for Indoor Mobile Telemetry," presentation, Jun. 21, 2005.

Pinto, "WMM-Wireless Mesh Monitoring," Technical report, 2009.

Sailhan et al., "Wireless Mesh Network Monitoring: Design, Implementation and Experiments, " In proc. of IEEE Workshop on Distributed Autonomous Network Management (DANMS), 2007.

(56) References Cited

OTHER PUBLICATIONS

Skibniewski et al, "Ubiquitous Computing: Object Tracking and Monitoring Inconstruction Processes Utilizing Zigbee™ Networks," The 23th International Symposium on Automation and Robotics in Construction (ISARC2006), Oct. 3-5, Tokyo, Japan.
Stewart, "Build reliable Zigbee-based solutions," EE Times-Asia, Apr. 16-30, 2007.
Texas Instruments, "Choose your ZigBee solution with TI," 1Q 2010.
Texas Instruments, "Consumer Medical Applications Guide," retrieved from the Internet: http://www.ti.com/medical, 2010.
Texas Instruments, "RF/IF and ZigBee® Solutions," http://focus.ti.com/analog/docs/gencontent.tsp? familyid=367 &genContentid=24190&DC . . . , Dec. 8, 2010.
Texas Instruments, "ZigBee® Wireless Networking Overview," 1 page, 2010.
The Silicon Horizon Inc., "techFX Zigbee rev A-techFX Zigbee Tools v 1.0," 2007-2008.
Tutorial-Reports.com, "Zigbee Tutorial," http://www.tutorial-reports.com/book/print/152, Nov. 1, 2010.
Unknown author, "The Nokia Network Monitor Introduction," http://www.panuworld.net/nuukiaworld/misc/netmon/index.htm, Oct. 30, 2005.
Versel, "ZigBee Alliance ratifies wireless protocol for low-power medical devices," retrieved from the Internet: http://www.fiercemobilehealthcare.com, Apr. 6, 2010.
Wellspring, "Router, Gateway, Base Station, Cell Modem Specification and Submittal," http://www.h2odegree.com/documents/ReferenceLibrary/OtherProductLiterature/RouterGatewayBaseSpecSheetSubmittal.pdf, 5 pages, prior to Jan. 2011.
Wellspring, "Wellspring Switches to a ZigBee-Cellular Hybrid System," press release, Feb. 20, 2006.
ZigBee Alliance, "ZigBee Wireless Sensor Applications for Health, Wellness and Fitness," https://docs.zigbee.org/zigbee-docs/dcn/09-4962.pdf, Mar. 2009.
Office Action; dated May 15, 2013; for U.S. Appl. No. 13/006,784; 37 pages.
Office Action dated May 22, 2013; for U.S. Appl. No. 13/037,886; 14 pages.
PCT Search Report and Written Opinion of the ISA; dated Mar. 15, 2013; for PCT Pat App. No. PCT/US2012/068895, dated, 15 pages.
PCT Search Report and Written Opinion of the ISA; dated Apr. 1, 2013; for PCT Pat. App. No. PCT/US2012/068892; 12 pages.
PCT Search Report and Written Opinion of the ISA; dated Apr. 1, 2013; for PCT Pat. App. No. PCT/US2012/068888; 15 pages.
PCT Search Report and Written Opinion of the ISA; dated Apr. 29, 2013; for PCT Pat. App. No. PCT/US2013/021530; 10 pages.
PCT International Preliminary Report on Patentability of the ISA; dated Sep. 12, 2013; for PCT Pat. App. No. PCT/US2012/025906; 14 pages.
Notice of Allowance; dated Oct. 9, 2013; for U.S. Appl. No. 13/037,886; 11 pages.
European Comments on Written Opinion dated Nov. 8, 2013; for EP Pat. App. No. 12708203.0; 2 pages.
Final Office Action dated Dec. 2, 2013; for U.S. Appl. No. 13/006,784; 38 pages.
Response filed Jul. 12, 2013; to Final Office Action dtaed May 22, 2013; for U.S. Appl. No. 13/037,886; 14 pages.
Office Action; dated May 15, 2013; for U.S. Appl. No. 13/006,784; 35 pages.
Article 19 Amendment; dated Nov. 16, 2012; for PCT Pat. App. No. PCT/US2012/021007; 7 pages.
Article 19 Amendment; dated Feb. 4, 2013; for PCT Pat. App. No. PCT/US2012/025906; 9 pages.
PCT International Preliminary Report on Patentability; dated Jul. 25, 2013; for PCT Pat. App. No. PCT/US2012/021007; 12 pages.
PCT International Search Report; dated Aug. 2, 2012; for PCT Pat. App. No. PCT/US2012/021008.
PCT International Preliminary Report on Patentability; dated Jul. 25, 2013; for PCT Pat. App. No. PCT/US2012/021008; 7 pages.

Miche, et al., "The Internet of Vehicles or the Second Generation of Telematic Services", ERCIM News, ERCIM, Paris, FR, vol. 77, Apr. 1, 2009, pp. 43-45.
Kawai et al., "Proposal of an Assured Corridor Mechanism for Urgent Information Transmission in Wireless Sensor Networks", IEICE Trans. on Commun., vol. E90B, No. 10, Oct. 1, 2007, pp. 2817-2826, XP001508610.
International Search Report and Written Opinion of the International Searching Authority for PCT/US2012/021007, dated Sep. 20, 2012, 19 pages.
International Search Report and Written Opinion of the International Searching Authority for PCT/US2013/020069, dated Feb. 1, 2013, 9 pages.
International Search Report and Written Opinion of the International Searching Authority for PCT/US2013/020071, dated Feb. 1, 2013, 10 pages.
International Search Report and Written Opinion of the International Searching Authority for PCT/US2012/025906, dated Dec. 3, 2012, 21 pages.
Office Action dated Nov. 16, 2012 for U.S. Appl. No. 13/037,886, filed Mar. 1, 2011, 19 pages.
Response to Office Action dated Nov. 16, 2012 for U.S. Appl. No. 13/037,886, filed Feb. 15, 2013.
Office Action dated Sep. 5, 2013, for U.S. Appl. No. 13/006,769, 36 pages.
European Response filed Mar. 3, 2014; to Official Communication dated Aug. 22, 2013; and to the Written Opinion; for European Pat. App. No. 12704944.3; 15 pages.
European Response filed Mar. 3, 2014; to Official Communication dated Aug. 22, 2013; and to the Written Opinion; for European Pat. App. No. 12701584.0; 11 pages.
PCT Search Report and Written Opinion of the ISA dated Mar. 4, 2014; for PCT Pat. App. No. PCT/US2013/059703; 12 pages.
Amendment filed Mar. 26, 2014, to Office Action dated Dec. 27, 2013; for U.S. Appl. No. 13/352,575; 12 pages.
Amendment and Response to Restriction Requirement for Office Action dated Feb. 10, 2014; filed Mar. 21, 2014; for U.S. Appl. No. 13/352,608; 7 pages.
Letter from CCPIT Patent and Trademark Law Office dated Mar. 3, 2014; for Chinese Pat. App. No. 201280011025.0; 1 page.
Chinese Voluntary Amendment (including English translation) received Mar. 3, 2014; for Chinese Pat. App. No. 201280011025.0; 16 pages.
Office Action dated May 27, 2014; for U.S. Appl. No. 13/334,463; 48 pages.
Mexican Notice of Allowance dated May 7, 2014; for Mexican Pat. App. No. MX/a/2013/009985; 2 pages.
Response filed Feb. 18, 2014 for Office Action dated Sep. 27, 2013 for U.S. Appl. No. 13/241,620; 24 pages.
Response filed Feb. 13, 2014 for Office Action dated Sep. 5, 2013 for U.S. Appl. No. 13/006,769; 18 pages.
Request for Continued Examination filed Jan. 24, 2014; for U.S. Appl. No. 13/037,886; 2 pages.
Response filed RCE on Feb. 13, 2014 for Final Office Action dated Dec. 2, 2013 for U.S. Appl. No. 13/006,784; 24 pages.
Office Action dated Dec. 27, 2013; for U.S. Appl. No. 13/352,575; 31 pages.
Notice of Allowance dated Apr. 30, 2014; for U.S. Appl. No. 13/241,620; 21 pages.
Office Action dated Apr. 29, 2014; for U.S. Appl. No. 13/352,608; 50 pages.
Mexican Official Action received May 2, 2014, for Mexican Pat. App. No. MX/A2013/008157; 3 pages.
U.S. Response to 312 Amendment dated Jul. 21, 2014; for U.S. Appl. No. 14/154,285; 3 pages.
Japanese Office Action (including English translation) dated Jun. 23, 2014; for Japanese Pat. App. No. 2013-549532 6 pages.
PCT International Preliminary Report on Patentability of the ISA dated Jul. 3, 3014; for PCT Pat. App. No. PCT/US2012/068892; 8 pages.
PCT International Preliminary Report on Patentability of the ISA dated Jul. 3, 2014; for PCT Pat. App. No. PCT/US2012/068888; 8 pages.

(56) References Cited

OTHER PUBLICATIONS

Singapore Written Opinion dated Jun. 18, 2014; for Singapore Pat. App. No. 2013053236; 11 pages.
Singapore Written Opinion dated Jun. 19, 2014; for Singapore Pat. App. No. 2013065230; 22 pages.
Response filed (with English Language Passage) of Mexican Office Action received Jul. 7, 2014; for Mexican Pat. App. No. MX/a/2013/008154; 16 pages.
European Search Report dated Jun. 14, 2014; for European Patent Application No. 14168075.1-1951; 8 pages.
Office Action dated Jun. 23, 2014 for U.S. Appl. No. 13/334,459, filed Dec. 22, 2011 44 pages.
Response with Terminal Disclaimer filed Jul. 30, 2014; to Office Action dated Jun. 20, 2014; for U.S. Appl. No. 13/334,447; 15 pages.
Response with Terminal Disclaimer filed Jul. 30, 3014; to Office Action dated Jun. 23, 2014; for U.S. Appl. No. 13/334,459; 13 pages.
Response filed Jul. 30, 3014; to Final Office Action dated Jun. 16, 2014; to U.S. Appl. No. 13/353,565; 22 pages.
Response filed Aug. 4, 2014; to Office Action dated May 27, 2014; for U.S. Appl. No. 13/334,463; 21 pages.
Mexican Response to Office Action received Jul. 29, 2014; for Mexican Pat. App. No. MX/a/2013/008157;14 pages.
PCT International Preliminary Report on Patentability dated Jul. 3, 2014; for PCT Pat. App. No. PCT/US2012/068895; 10 pages.
Final Office Action dated Aug. 6, 2014; for U.S. Appl. No. 13/352,608; 38 pages.
PCT International Preliminary Report on Patentability of the ISA dated Jul. 31, 2014; for PCT Pat. App. No. PCT/US2013/020069; 6 pages.
PCT international Preliminary Report on Patentability of the ISA dated Jul. 31, 2014; for PCT Pat. App. No. PCT/US2013/020071; 6 pages.
Singapore Written Opinion dated Jul. 25, 2014; for Singapore Pat. App. No. 2013053244; 7 pages.
Japanese Office Action dated May 30, 2014 for Application No. 2013-549531.
Notice of Allowance for U.S. Appl. No. 13/352,575, filed Jan. 18, 2012.
Office Action dated Jun. 20, 2014 for U.S. Appl. No. 13/334,447, filed Dec. 22, 2011.
Mexican Office Action received Apr. 22, 2014; for Mexican Pat. App. No. MX/a/2013/008154; 4 pages.
Response to Office Action dated Apr. 29, 2014 for U.S. Appl. No. 13/352,608, filed Jan. 18, 2012.
Notice of Allowance dated Jun. 6, 2014 for U.S. Appl. No. 14/154,285, filed Jan. 14, 2014.
Notice of Allowance dated Jun. 9, 2014 for U.S. Appl. No. 13/006,769, filed Jan. 14, 2011.
U.S. Appl. No. 14/308,881, filed Jun. 19, 2014, Gaines, et al.
Notice of Allowance dated Sep. 22, 2014; for U.S. Appl. No. 13/006,784; 47 pages.
Mexican Memo Concerning the Official Action dated Sep. 19, 2014; regarding Mexican Office Action for Mexican Patent Application No. MX/A/2013/008157; 1 page.
Japanese Amendment and Argument with Claims and Argument in English dated Sep. 22, 2014; for Japanese Pat. App. No. 2013-549532; 28 pages.
Russian Office Action (with Engiish Summary) dated Oct. 28, 2014; for Russian Pat. App. No. 2014124988/20(040628); 3 pages.
Singapore Response to Written Opinion dated Nov. 18, 2014; for Singapore Pat. App. No. 2014/268260258W; 15 pages.
Australian Examination Report dated Oct. 28, 2014; for Australian Pat. App. No. 2012223646; 5 pages.
Singapore Response to Written Opinion dated Nov. 18, 2014; for Singapore Pat. App. No. 2014/269351479S; 21 pages.
Australian Patent Examination Report No. 1 dated Nov. 11, 2014; for Australian Pat. App. No. 2013205134; 3 pages.
Singapore Amendment dated Sep. 12, 2014; for Singapore Pat. App. No. 11201403379U; 23 pages.
Japanese Notice of Reasons for Rejection dated Nov. 5, 2014; for Japanese Pat. App. No. 2013-556717; 8 pages.
Singapore Response to Written Opinion dated Nov. 18, 2014; for Singapore Pat. App. No. 2013065230; 21 pages.
South African Amendment dated Nov. 27, 2014; for South African Pat. App. No. 2013/05094; 9 pages.
Chinese Voluntary Amendment with PPH received Dec. 16, 2014; for Chinese Pat. App. No. 201280063960.1; 26 pages.
Chinese Voluntary Amendment with PPH received Dec. 17, 2014; for Chinese Pat. App. No. 201280063534.8; 25 pages.
Australian Response filed Dec. 16, 2014; for Australian Pat. App. No. 2012205515; 20 pages.
Korean Letter to Kim & Chang dated Dec. 5, 2014; for Korean Pat. App. No. 10-2013-7018317; 10 pages.
Korean Argument and Amendment filed Dec. 12, 2014; for Korean Pat. App. No. 10-2013-7018317; 23 pages.
U.S. Response to 312 Amendment received Dec. 26, 2014; for U.S. Appl. No. 14/154,285; 7 pages.
Australian Patent Examination Report dated Nov. 18, 2014; for Australian Pat. App. No. 2012205516; 3 pages.
South African Notification of Acceptance dated Dec. 10, 2014; for South African Pat. App. No. 2013/05094; 1 pages.
Australian Patent Examination Report No. 1 dated Sep. 1, 2014; for Australian Pat. App. No. 2012205515; 3 pages.
European Search Report dated Sep. 18, 2014; for European Pat. Ap. No. 14167899.5; 9 pages.
Canadian Office Action dated Aug. 8, 2014; for Canadian Pat. App. No. 2,823,700; 7 pages.
Response to Final Office Action filed Oct. 3, 2014; to Office Action dated Aug. 6, 2014; for U.S. Appl. No. 13/352,608; 12 pages.
Request for Continued Examination filed Oct. 3, 3014; for U.S. Appl. No. 13/352,608; 2 pages.
Australian Examiner's Report dated Sep. 1, 2014; for Australian Pat. App. No. 2012205515; 3 pages.
Korean Notice of Preliminary Rejection, includng English translation, dated Oct. 21, 2014; for Korean Pat. App. No. 10-2013-7018317; 7 pages.
Microvision, Inc., Product literature for Microvision Wearable Displays, available at www.microvision.com, copyright 1996-2009, 5 pages.
Eurotech Group, Zypad WR11xx—Rugged Wearable Computer, Product Announcement, available at http://www.zypad.com/zypad/news.aspx?pg=news&id=99, Nov. 17, 2008, 1 page.
Eurotech Group, Zypad WL1000 detasheet, available at http://www.eurotech.com/downloadarea/Datasheets/Wearable%20Computers/Zypad%20WL%201000_sf.pdf, undated, 2 pages.
Eurotech Group, Zypad WR11XX data sheet, available at http://www.eurotech.com/downloadarea/Datasheets/Wearable%20Computers/Zypad%20WR1100_sf.pdf, undated, 4 pages.
Eurotech Group, Zypad WL1100 data sheet, available at http://www.eurotech.com/downloadarea/Datasheets/Wearable%20Computers/Zypad%20WL%201100_sf.pdf, possibly dated Sep. 9, 2008, 2 pages.
Corventis, Inc., Product literature—Wireless cardiovascular solutions for continuous patient surveillance, available at http://corventis.com/US/medprof.asp, copyright 2009, 1 page.
Corventis, Inc., Product literature for NUVANT Mobile Cardiac Telemetry (MCT) System, available at http://corventis.com/US/nuvant.asp copyright 2009, 2 pages.
Corventis, Inc., Product literature for AVIVO Mobile Patient Management (MPM) System, available at http://corventis.com/US/avivo.asp, copyright 2009, 2 pages.
Notice of Allowability dated Oct. 31, 2004; for U.S. Appl. No. 13/334,447; 10 pages.
Mexican Response to Office Action received Nov. 3, 2014; for Mexican Pat. App. No. MX/a/2013/008157; 12 pages.
South African Amendment dated Oct. 31, 2014; for South African Pat. App. No. 2014/04810; 10 pages.
Gaines et al, "Improved Wireless Relay Module for Remote Monitoring Systems;" U.S. Appl. No. 14/308,881, filed Jun. 19, 2014; 36 pages.

(56) References Cited

OTHER PUBLICATIONS

Canadian Office Action dated Aug. 4, 2014; for Canadian Pat App. No, 2,823,600; 3 pages.
PCT Search Report and Written Opinion of the ISA dated Apr. 29, 2013; for PCT Pat. App. No. PCT/US2013/021530; 10 pages.
U.S. Appl. No. 14/462,025, filed Aug. 18, 2014, Wiesner et al.
Notice of Allowance dated Aug. 20, 2014, for U.S. Appl. No. 13/334,447; 25 pages.
Notice of Allowance dated Aug. 15, 2014; for U.S. Appl. No. 13/334,459; 20 pages.
PCT International Preliminary Report on Patentability and Written Opinion of the ISA dated Jul. 31, 2014; for PCT Pat. App. No. PCT/US2013/021530; 8 pages.
Singapore Request for Combined Search and Examination Report, including English Specification, filed Aug. 29, 2014; for Singapore Pat. App. No. 11201403422P; 8 pages.
Russian Office Action dated Oct. 16, 2014; for Russian Pat. App. No. 2013121827/08' 4 pages.
Final Office Action dated Jan. 2, 2015; for U.S. Appl. No. 13/334,463; 48 pages.
Singapore Supplemental Search Report dated Dec. 8, 2014; for Singapore Pat. App. No. 2013065230; 8 pages.
Singapore Response to Written Opinion dated Dec. 31, 2014; for Singapore Pat. App. No. 2013053244; 19 pages.
European Response to Rule 161(2) and 162 EPC filed on Dec. 30, 2014; for European Pat. App. No. 12861028.4; 14 pages.
Singapore Request to Amend Application Before Grant filed on Jan. 15, 2015; for Singapore Pat. App. No. 11201404126W; 8 pages.
Australian Notice of Acceptance dated Jan. 15, 2015; for Australian Pat. App. No. 2012205515 2 pages.
Singapore Search and Examination Report dated Dec. 23, 2014; for Singapore Pat. App. No. 2013053236; 4 pages.
Singapore Request to Amend Application Before Grant dated Jan. 16, 2015; for Singapore Pat. App. No. 11201404133R; 18 pages.

* cited by examiner

US 9,020,419 B2

WIRELESS RELAY MODULE FOR REMOTE MONITORING SYSTEMS HAVING POWER AND MEDICAL DEVICE PROXIMITY MONITORING FUNCTIONALITY

RELATED APPLICATION

This application is a continuation-in-part application of co-pending U.S. patent application Ser. No. 13/334,463 entitled "Wireless Relay Module for Remote Monitoring Systems Having Alarm And Display Functionality" filed Dec. 22, 2011, which is related to co-pending U.S. patent application Ser. No. 13/006,769 entitled "Wireless Relay Module for Remote Monitoring Systems" filed Jan. 14, 2011, each of which shares an assignee-in-common with the present application and is incorporated by reference in its entirety herein for all purposes. This application is also related to co-pending U.S. Application Ser. No. 13/006,784, entitled "Medical Device Wireless Network Architectures" filed Jan. 14, 2011, which shares an assignee-in-common with the present application is incorporated by reference in its entirety herein for all purposes.

FIELD OF THE INVENTION

The present application is directed to networked communications between medical devices and remote monitoring devices via wireless relay networks and/or internet-accessible wireless communications networks having power and medical device proximity monitoring capabilities.

BACKGROUND OF THE INVENTION

In critical care and home care health service centers including hospitals, clinics, assisted living centers and the like, caregiver-patient interaction time is at a premium. Caregivers are needed to respond rapidly to significant health conditions because any delay can be the difference between life and death. Systems of centralized monitoring have been developed to assist caregivers by transmitting physiological data from each patient (or from geographically-dispersed critical care health service centers) to a centralized location.

At this centralized location, a single or small number of technicians monitor all of this patient information to determine patient status. Information indicating a patient alarm condition will prompt the technicians and/or system to communicate with caregivers to provide immediate patient attention, for example via wireless pagers and/or cell phones, and/or by making a facility-wide audio page.

The information transmitted to the centralized location could be performed over a local area network, such as with a "WiFi" network based on IEEE 802.11 standards. The problem, however, with this network is that it is often difficult to secure sufficient local area network access for the purpose of providing centralized monitoring. Moreover, when a patient is located remotely from a critical care health service center (e.g., at home), access to traditional local area network facilities such as a WiFi network may be unavailable or not sufficiently reliable to support critical care monitoring applications.

An alternative to using WiFi is ZIGBEE, based on the IEEE 802.15.4 standard for wireless personal area networks. The ZIGBEE networks have previously been used for collecting information from a variety of medical devices in accordance with IEEE 11073 Device Specializations standard for point-of-care medical device communication, include for example pulse oximeters, blood pressure monitors, pulse monitors, weight scales and glucose meters. See, e.g., *ZIGBEE Wireless Sensor Applications for Health, Wellness and Fitness*, the ZIGBEE Alliance, March 2009, which is incorporated by reference herein in its entirety for all purposes.

The advantages of ZIGBEE networks are that the network is dynamically configurable (e.g., "self-healing" mesh configurations) and operates with low power requirements (e.g., enabling ZIGBEE transceivers to be integrally coupled to the medical devices under battery power). In addition, ZIGBEE networks generally require shorter, less cumbersome passwords for secure network access that are used for securely accessing WiFi networks (for example, the wired equivalent privacy or "WEP" passwords used in WiFi networks. However, transmission ranges between individual ZIGBEE transceivers are generally limited to no more than several hundred feet. As a consequence, ZIGBEE networks are generally unusable for centralized monitoring locations located off-site, or for conditions in which a patient may be ambulatory and the distance between a medical device with a ZIGBEE transmitter and the ZIGBEE receiver may vary and at times extend beyond several hundred feet.

The remote monitoring system may be provided with an intermediate device (wireless relay module) that receives medical device data from a medical device via a WiFi or ZIGBEE network, and that relays this information to the centralized location via an internet-accessible wide area network (WAN) such as a cellular network.

SUMMARY OF THE INVENTION

It would be desirable to provide a wireless relay that can monitor a characteristic of a power source of the module, and transmit an alarm upon detecting a change in the characteristic. In addition, it would be desirable to provide a wireless relay that can monitor a characteristic of the an associated medical device, and transmit an alarm upon detecting a change in this characteristic.

The present invention is directed to wireless relay modules for enabling alarm recognition and display alerts in networked communications between a series of medical devices and remote monitoring devices via wireless relay networks and/or internet-accessible wireless communications networks. In some embodiments, the wireless relay module comprises a display, a receiver capable of wirelessly receiving medical device data over a wireless relay network from at least one medical device along with a first transmitter capable of wirelessly transmitting medical device data to a second wireless relay module over the wireless relay network, and a second transmitter capable of wirelessly transmitting data over an internet-accessible wireless communication network. It is possible for the transmitters and receivers to be implemented as transceivers.

"Medical device data" as generally used herein means data from or about the medical device including, for example, medical device identification, medical device software, medical device settings or status information (including alarm information and/or alarm priority), medical device location information (including for example global positioning system (GPS) coordinates), patient identification information, patient personal identification number(s) "PIN(s)", patient prescriptions, and/or patient medical and/or physiological data as is collected, produced and/or generated by at least one of the medical device and patient identification device; as well as wireless relay network information such as location or status information.

A controller is typically coupled to the first and second transmitters, and controls the wireless relay module to select one of said first or second transmitter for transmitting medical device data received by the receiver over one of the two respective networks. The controller is further capable of producing an alarm signal upon a changed characteristic of a power source for the wireless relay module. The changed characteristic may include, for example, a loss of commercial alternating current ("AC") power supplied to the wireless relay module.

The wireless relay module may preferably include a battery back-up circuit as a secondary source of power and/or as a primary power source in the event of an AC power failure or interruption. In this case, a changed characteristic of the power source may include a "low battery" condition (as evidenced, for example, by measuring a moderate degradation in battery voltage) and/or a "near dead condition (as evidenced, for example, by measuring a severe degradation in battery voltage). In the event of a near dead condition, the controller may further be capable of storing wirelessly-received medical device data in a memory of the wireless relay module.

In another embodiment, the controller may be further capable of producing an alarm signal upon a changed characteristic of a medical device. For example, the controller may be capable of generating an alarm in the event that the medical device fails to respond to a request for response transmitted by the first transmitter to the medical device. In addition, the controller may be capable of generating an alarm according to a characteristic of the medical device data transmitted by the medical device to the wireless relay module (for example, including a degradation in signal strength of the wireless signals carrying medical device data and/or a degradation in the data rates of these wireless signals).

Each of the wireless relay module and an associated medical device may be equipped with a location device (for example, a global positioning system (GPS) device) such that a change in the distance between the medical device and the wireless relay module can be determined. In this case, the controller may preferably be capable of generating an alarm when that distance increases to a point where communications between the medical device and the wireless relay module may be compromised.

In yet a further embodiment, a speaker is coupled to the controller, where the speaker is capable of providing an audible alert, e.g., speech or other sounds, of the alarm condition. It is contemplated in accordance with the invention that the volume or type of such audible alert is indicative of a type or severity of the alarm condition. Moreover, an alternative embodiment of the wireless relay module includes a microphone and speaker to facilitate voice communication between a caregiver proximate the wireless relay module and a clinician or technician at a remote monitoring device.

BRIEF DESCRIPTION OF THE DRAWINGS

The invention will become more readily apparent from the Detailed Description of the Invention, which proceeds with reference to the drawings, in which.

DETAILED DESCRIPTION OF THE INVENTION

Reference will now be made in detail to exemplary embodiments of the invention. Examples of these exemplary embodiments are illustrated in the accompanying drawings. While the invention is described in conjunction with these embodiments, it will be understood that it is not intended to limit the invention to the described embodiments. Rather, the invention is also intended to cover alternatives, modifications, and equivalents as may be included within the spirit and scope of the invention as defined by the appended claims.

In the following description, specific details are set forth in order to provide a thorough understanding of the present invention. The present invention may be practiced without some or all of these specific details. In other instances, well-known aspects have not been described in detail in order not to unnecessarily obscure the present invention.

For the purpose of illustrating the present invention, exemplary embodiments are described with reference to FIGS. 1 through 8.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Figure 1A:
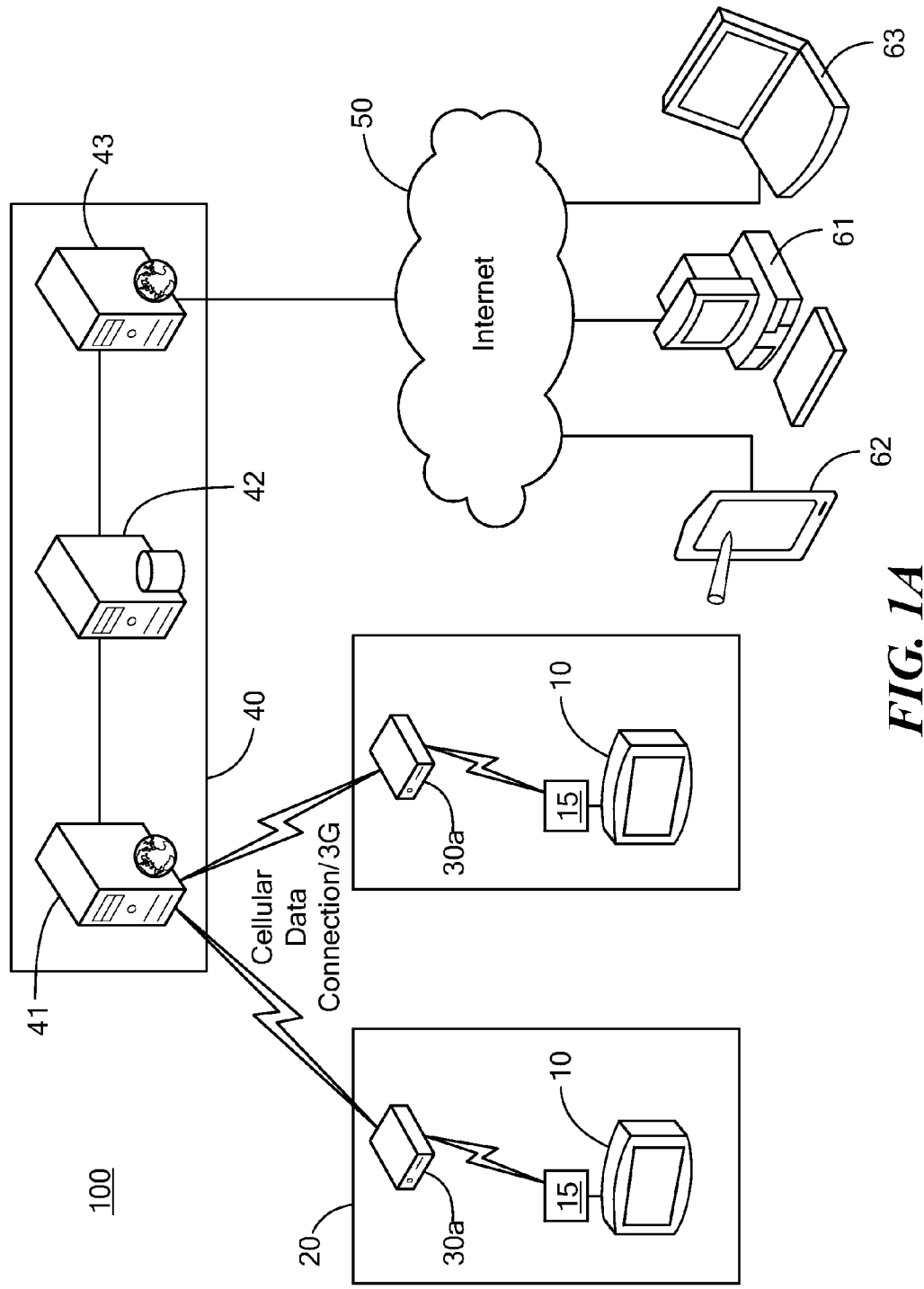
FIG. 1(a) presents a schematic diagram of an exemplary architecture for a system for monitoring medical devices according to the present invention.

A schematic diagram of an exemplary architecture 100 for a system for monitoring medical devices in accordance with the present invention is illustrated in FIG. 1(a). One or more medical devices 10 are provided at a patient facility 20 for monitoring the medical condition and/or administering medical treatment to one or more patients. Patient facility 20 may comprise a critical care health service center (for example, including hospitals, clinics, assisted living centers and the like) servicing a number of patients, a home facility for servicing one or more patients, a mobile medical car vehicle or vessel, or a personal enclosure (for example, a backpack) that may be attached to or worn by an ambulatory patient. Associated with each medical device 10 is an interface circuit 15 that includes a transceiver for transmitting and receiving signals in a facility-oriented wireless network such as, for example, a Low-Rate Wireless Personal Area Network or "LR-WPAN," ZIGBEE network or other low-power personal area networks such as the low power Bluetooth networks, e.g., Bluetooth 4.0, existing or presently under development or consideration. It should be understood that interface circuit 15 may be contained within or disposed external to medical device 10 in accordance with the present invention. Also provided within the patient facility 20 are one or more relay modules 30a.

Figure 1B:
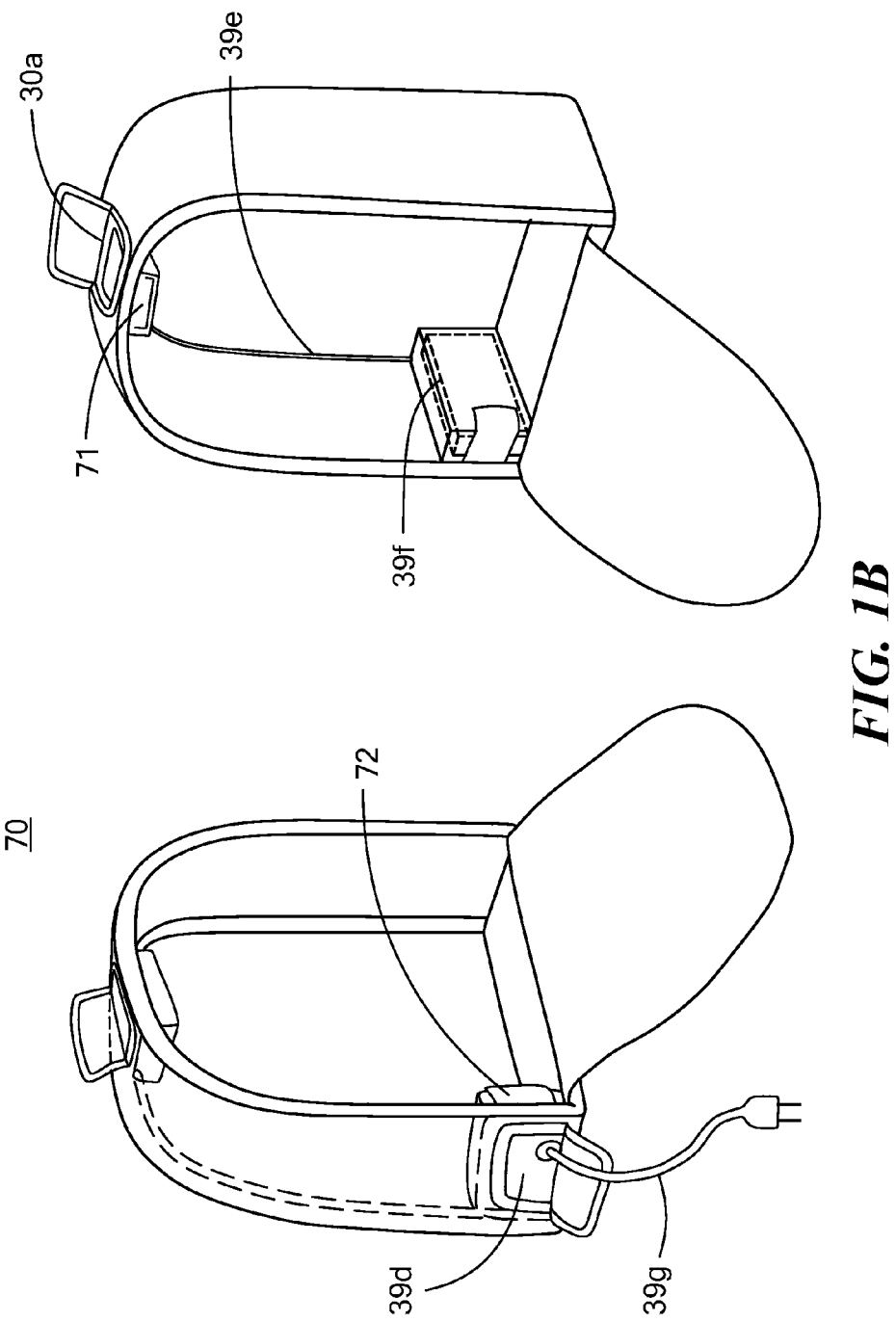
FIG. 1(b) presents a schematic diagram of an exemplary backpack for carrying components of the exemplary architecture according to the present invention.

FIG. 1(b) illustrated an exemplary backpack 70 as may be suitable for use as a personal enclosure. The backpack 70 includes a pouch 71 for housing a relay module 30a, a pouch 72 for housing a power and charging circuit 39d for providing power to the relay module 30a, and a power cord 39e for supplying power from the power and charging circuit 39d to the relay module 30a. As depicted, the power and charging circuit 39d includes a battery compartment 39f, and a charging circuit (not shown) and a power cord 39g for providing external commercial AC power to the power and charging circuit 39d in order to charge batteries in the battery compartment 39f. One of ordinary skill in the art will readily appreciate that the exemplary backpack 70 provides but one of a number of suitable backpack arrangements as contemplated by the present invention.

As illustrated in FIG. 1(a), a suitable access point 40 useable with the present invention may include an inbound web server 41 that incorporates or otherwise has access to a transceiver for communicating with the relay modules 30a over a cellular data connection or or other wireless wide-area network ("WWAN"). Medical device data received by the inbound web server 41 over the WWAN is forwarded to a secure data storage server 42, which is configured for example to log the medical device received data in association with identification information of the respective medical devices. "Medical device data" as generally used herein means data from or about the medical device including, for example, medical device identification, medical device software, medical device settings or status information (including alarm information and/or alarm priority), medical device location information (including for example global positioning system (GPS) coordinates), patient identification information, patient personal identification number(s) "PIN(s)", patient prescriptions, and/or patient medical and/or physiological data as is collected, produced and/or generated by at least one of the medical device and patient identification device; as well as wireless relay network information such as location or status information.

An outbound web server 43 associated with access point 40 can be configured, for example, to receive and qualify data retrieval requests submitted by one or more of remote monitoring devices 61, 62 and 63 over a broad-band network 50 (for example, over the Internet), to request associated medical device data to be retrieved from the secure data storage server 42, and to format and transmit the retrieved data to the one or more remote monitoring devices 61, 62 and 63 for display on associated device displays. While this disclosed architecture for the access point 40 is illustrated with an exemplary embodiment of the present invention, it should be understood that any architecture for the access point 40 that enables the receipt, storage and retrieval of medical device data on a device display of the one or more remote monitoring devices 61, 62 and 63 is intended to be included within the scope of the present invention. For example, storage server 42 may be integrated into the outbound web server 43. Further alternative configurations may for example involve a plurality of mirror storage servers 42 each storing medical device data, and accessible as a plurality of outbound web servers 43.

Figure 2:
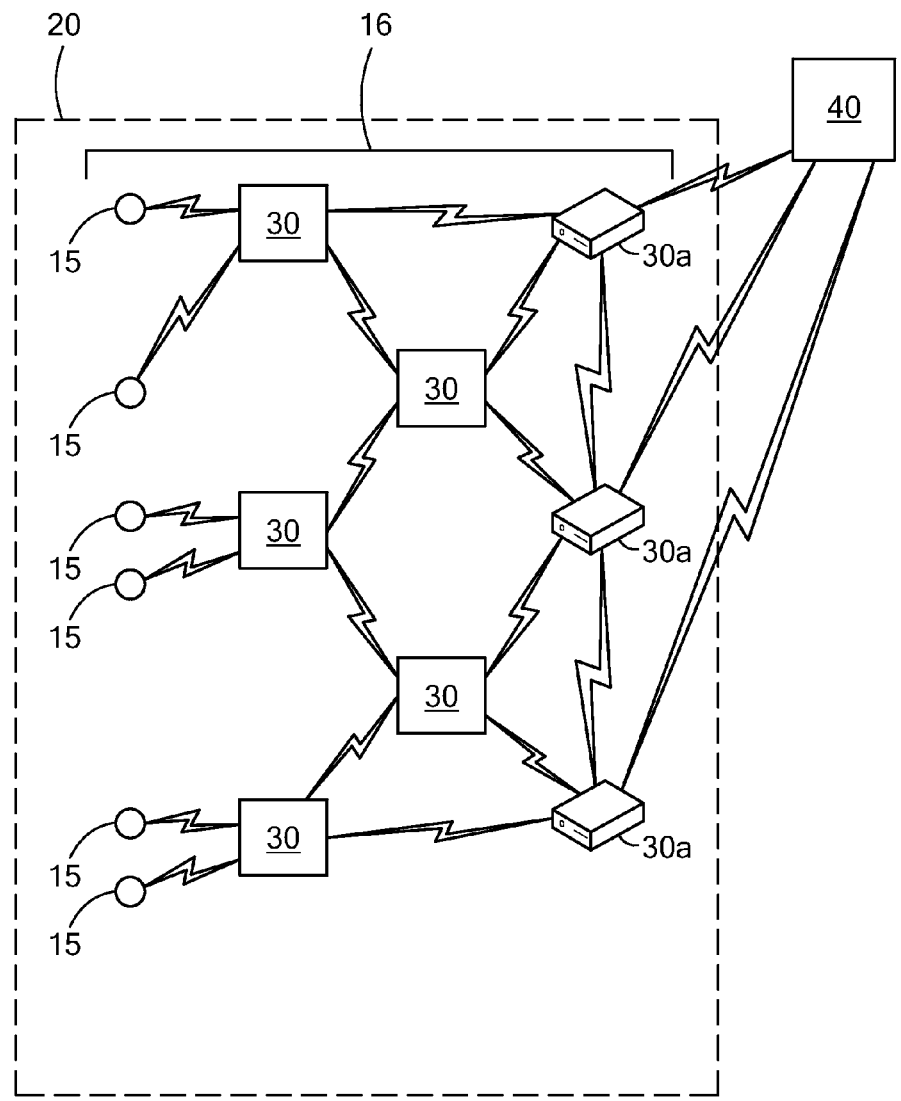
FIG. 2 presents a schematic diagram further illustrating exemplary wireless network components of the architecture according to the present invention.

FIG. 2 presents a block diagram that further illustrates exemplary components of the architecture that are located within or otherwise associated with the patient facility 20 of FIG. 1. In FIG. 2, a number of interface circuits 15 and relay modules 30, 30a are arranged in a mesh network 16 within the patient facility 20. The interface circuits 15 and relay modules 30, 30a are configured to communicate with one another via associated wireless links. In a preferred embodiment of the present invention represented in FIG. 2, the network 16 is a ZIGBEE mesh network based on the IEEE 802.15.4 standard. However, the network 16 may be organized according to a variety of other wireless local area network (WLAN) or WPAN formats including, for example, WiFi WLANs based on the IEEE 802.11 standard and Bluetooth WPANs based on the IEEE 802.15.1 standard.

In FIG. 2, each relay module 30 includes a first transceiver (illustrated in FIG. 3 as first transceiver 31 of relay module 30a) for receiving signals from and transmitting signals to the interface circuits 15 in the facility-oriented wireless network discussed above. Relay modules 30a further include a second transceiver 32 for wirelessly transmitting signals to and receiving signals from an access point 40 via a WWAN. Suitable WWANs for use with the present invention include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of the International Telecommunication Union Radiocommunication Sector (ITU-R). See, e.g., Vijay Garg, *Wireless Communications & Networking*, Morgan Kaufmann 2007, which is incorporated by reference herein in its entirety. Additional suitable exemplary WWANs include metropolitan area networks (MANs), campus area networks (CANs), local area networks (LANs), home area networks (HANs), personal area networks (PANs) and body area networks (BANs). For compliance with Health Insurance Portability and Accountability Act of 1996 (HIPAA) regulations and other domestic and/or international privacy laws or regulations, communications over each of the facility-oriented wireless network and WWAN are preferably conducted securely using, for example, using a Secure Sockets Layer (SSL) protocol or a Transport Layer Security (TLS) protocol.

In the illustrated ZIGBEE mesh network 16 of FIG. 2, each of the interface circuits 15 includes a communications interface such as, for example, a wired communications interface connected or in communication with to an associated medical device 10. In addition, each of the relay modules 30, 30a includes at least one transceiver 31 configured to communicate with other relay modules 30, 30a in the ZIGBEE mesh network 16. Relay modules 30a further include at least a second transceiver 32 for communicating over the WWAN with the access point 40. Each of the transceivers 31, 32 will typically include a transmitter for transmitting medical device data over one of the mesh network 16 or the WWAN, and a received for receiving medical device data transmitted over one of the mesh network 16 or the WWAN.

The representative ZIGBEE mesh network 16 provides the advantages of being self-configurable when one or more interface circuits 15 and/or relay modules 30, 30a are added to the network, and may be self-healing when one or more interface circuits 15 and/or relay modules 30, 30a are removed from or otherwise disabled in the network. Subgroupings of the interface circuits 15 and relay modules 30, 30a may be provided in a defined geographic space (for example, on an individual floor or within a region of a floor in a multi-floor home or care facility).

Figure 3:
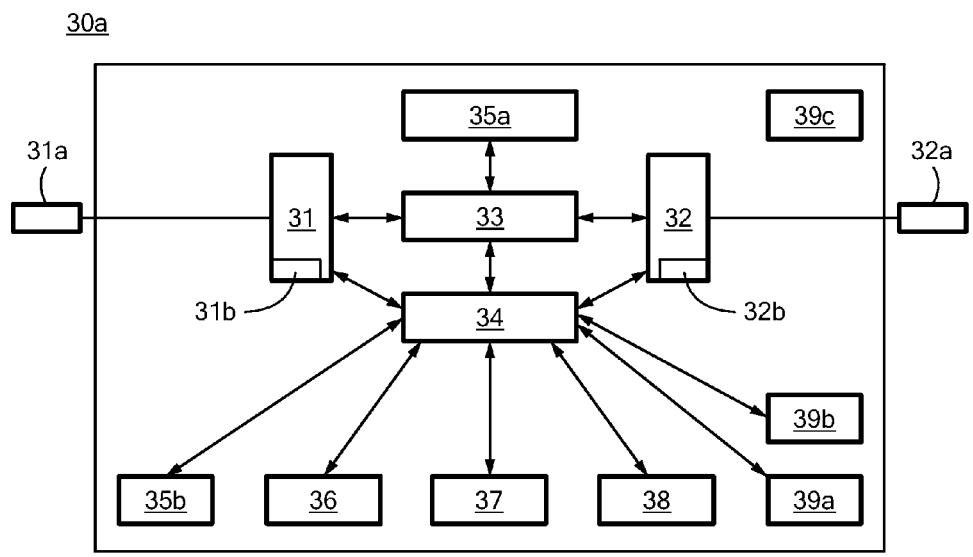
FIG. 3 presents a schematic diagram illustrating an exemplary wireless relay module associated with the architecture according to the present invention.

FIG. 3 provides a block diagram illustrating exemplary components of relay module 30a. In FIG. 3, the relay module 30a includes a first transceiver 31 for wirelessly communicating with interface circuits 15 and other relay modules 30, 30a in the WLAN or WPAN 16 of FIG. 2 via an antenna 31a. A transceiver as contemplated in this description may include a receiver and/or transmitter. The relay module 30a further includes a second transceiver 32 for wirelessly communicating with the access point 40 over the WWAN via an antenna 32a. Each of the transceivers 31, 32 is in communication with a data processing circuit 33, which is configured to operate under the control of a controller, e.g., processor 34, to accept medical device data received by the transceivers 31, 32 and store the received data in a buffer element 35a.

In addition, the data processing circuit 33 is further configured to retrieve data from the buffer element 35a under the direction of the processor 34 and provide the retrieved data to a selected one of the transceiver 31 or transceiver 32 for transmission. Further embodiments can for example involve one or more processors 34 configured to accept medical device data from mesh network 16 and to send the medical device data through the WWAN without storing the medical device data in the relay module 30a In order to make a selection, the processor 34 is configured to communicate with respective status modules 31b, 32b of the transceivers 31, 32 in order to determine a communications status of each of the transceivers 31, 32. The processor is also configured to communicate with a memory 35b, which may for example store a stored program for operating the processor 34 as well as certain other data as further described herein The relay module 30a of FIG. 3 further preferably includes a location device 39a including, for example, a conventional global positioning system signal ("GPS") chip for determining a GPS location of the relay module 30a. In addition, the relay module 30a of FIG. 3 includes a power monitoring device 39b for monitoring a voltage level of a external AC power source (not shown) providing power to the relay module 30a, and a secondary power source 39c comprising for example non-rechargeable lead-acid batteries, rechargeable lithium-ion batteries or other conventional rechargeable energy storage devices for providing a secondary power source to the relay module 30a, or a primary power source in the event of a failure of the external AC power source. Alternatively and/or additionally, the power monitoring device may for example monitor a sensor for detecting a disconnection of the external AC power supply by mechanical means (for example, using a spring-loaded push-pin switch that disengages when an associated AC plug of the relay module 30,30a is removed from an external AC receptacle), by electronic means (for example, using an inductive sensor incorporated in proximity to the AC power plug) and the like.

The processor 34 may be a single dedicated processor, a single shared processor, or a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be implemented in one or more configurations of embodiments of the invention.

In accordance with the present invention, the medical device data received by one of the transceivers 31, 32 from the one or more medical devices 10 may include, for example, information indicative of an alarm condition. In addition to the types of medical device data previously provided herein, exemplary received information may include, for example, at least one of medical device description, medical device identification (e.g., unique device number), medical device location (e.g., device/patient room number), patient identification (e.g., patient identification number), alarm type, alarm error code, and/or alarm severity. Exemplary methods in which an alarm condition may be determined include predetermined codes, look-up table(s) and or algorithms for identifying alarm conditions based on processing the received information.

In addition to information indicative of an alarm condition contained in the medical device data received from one or more medical devices 10, it is also possible to receive the alarm indication from another relay module and/or as a result of an indication internally generated in the relay module 30a itself. For example, the relay module 30a could receive such information from another relay module when the other relay module malfunctions. In this way, it is assured that the relay module 30a provides the necessary redundancy for another relay module. Additionally, it is further possible for such information to be transmitted to the relay module 30a from the other relay module when the information is indicative of a high severity alarm condition, e.g., a significant medical emergency, such as emergency 911. Such redundancy will enable a sufficient number of caregivers to be notified of the emergency condition through multiple relay modules to facilitate a prompt response.

In another exemplary implementation, the relay module 30a may be notified if another relay module is experiencing numerous alert conditions associated with other modules or medical devices and communicate the alarm information to caregivers. If this occurs, the other relay module may, for example, divert the information indicative of an alarm to the relay module 30a using the WLAN or WPAN 16. The particular relay module 30a selected to receive the alarm information from the other relay module may be based on many factors such as, for example, relay module location, relay module availability, number of caregivers at a given location and/or floor, defined master/slave relationships among the relay modules 30a, and the like.

In another embodiment, it is possible that the information indicative of an alarm condition is received at the relay module 30a, but for some reason, such as a malfunction and/or data transmission bottleneck, the alarm is never communicated audibly and/or visually to the caregivers. To prevent this occurrence, the relay module 30a can be configured to transmit a message back to the one or more medical devices 10 confirming that an alarm was presented to the caregiver. If the message is not received within a predetermined amount of time by the one or more medical devices 10, then one or more medical devices 10 may attempt to communicate with other relay modules to ensure the alarm is addressed. Similar factors, e.g., location, availability, number of caregivers, etc., as described above may be used to select the other relay module(s) for providing alerts for the one or more medical devices.

In a further embodiment, the relay module 30a may internally generate its own alarm and/or device signals in relation to the relay module 30a, for example, the current status of the relay module 30a (e.g., external AC power loss) and/or current communication or connection status (e.g., status with the WLAN or WPAN 16 or WWAN).

After identifying that received data is indicative of an alarm condition, the processor 34 of FIG. 3 may transmit a message containing alarm information including, for example, at least one of medical device description, medical device identification, medical device location, patient identification, alarm type, alarm error code, and/or alarm severity, to a display 36 attached to the relay module 30a. In this way, an alarm alert may mirror an alarm alert emitted by the originating medical device. The particular type of display chosen for use with the relay module 30a is not critical for practicing any of the aspects of the present invention. Accordingly, it is possible for display 36 to be a monochrome or color dot matrix, LCD, LED or other display device. Alternatively and/or in addition, the processor 34 may transmit the message containing alarm information to a medical device 10 via the transceiver 31, and/or to the access point 40 via the transceiver 32.

In addition, the processor 34 may also employ a speaker 37, such as a loudspeaker, coupled to the relay module 30a to emit an audible alert indicative of the alarm condition. It is possible for the audible alert based on the alarm condition to be at least one of volume, pitch, tone, type, audible sequence or duty cycle, or recorded sound to indicate the type, urgency or severity of the alarm condition. It is advantageous for an alarm indicating a life-threatening emergency to be more attention-getting, e.g., loud siren, than alarms for less significant conditions that may be addressed by, for example, beeps or calmer tones.

It is also possible for the emitted audible alerts to be spoken words, commands, tones or other sounds. In this way, if the alert emitted from the one or more medical devices 10 is not directly addressed, then the relay module 30a alarm sounds should alert any caregivers located outside of the patient's room. The processor 34 may also in accordance with the invention cause a signal to be transmitted by, for example, the first transceiver 31 over the WLAN or WPAN 16 to one or more devices including, for example, PDAs, cell phones, pagers, and tablets. In addition, the alarm information may be transmitted over the WWAN using the second transceiver 32 to the one or more devices.

In addition, an input/output circuit 38 may be electrically connected to, for example, user-actuatable buttons, dials or input mechanisms associated with the relay module 30a. Using these buttons, dials, or input mechanisms, the audible alerts produced by the relay module 30a may be muted, i.e., disabled, or volumes substantially reduced. The muting or volume reduction may alternatively be in response to the relay module 30a receiving a signal from the originating medical device transmitting the information, such as in response to a caregiver acknowledging that the emergency condition is being addressed by entering the proper inputs to the originating medical device. Such acknowledgements may preferably take the form of corresponding acknowledgement codes each associated with a particular alarm condition. Even with the audible alerts muted or otherwise disabled, it may be advantageous to continue displaying the alerts on the display 36. The display 36 may continue to display alerts until likewise the alert condition is extinguished or confirmation from a caregiver at the originating medical device or the relay module 30a is received.

In accordance with another aspect of the invention, the processor 34 may control the display 36 to alternate or cycle displayed information intermittently with information from a single medical device or multiple medical devices. For instance, the processor 34 may cause a visual alarm alert indicating an alarm condition (based upon a portion of medical device data) from a first medical device to be shown on the display 36, for example, for a time period of between 2 to 30 seconds before displaying information for another medical device. The visual alarm alerts corresponding to higher severity alarm conditions may be shown for longer durations than alerts of for lower severity alarm conditions. Also, the type of alarm condition may further dictate the display length of time for visual alarm alerts or other information from a particular medical device. Additionally, the processor 34 may also or alternatively display on the display 36 the number of medical devices communicating information indicative of alarm conditions to the relay module 30a and/or show a description of such devices.

In addition, it is possible for the display 36 to display the alerts in different foreground or backlight colors, such as green backlight for normal operation or red backlight for alarm situations, to use color representing the respective severities of alarm conditions. It is further possible for the colors to correspond to specific alarm conditions (e.g., low glucose level) and/or general groups of conditions (e.g., heart conditions). The display may alternatively or in addition incorporate, for example, a multi-colored light-emitting diode array to display the status of the medical devices.

The display 36 may also be used to display non-alarm related information including, for example, internal power supply charge level or status, software version, software download status, relay module network status, handshake status and signal strength of the received WLAN or WPAN 16, and/or WWAN signals. Displayed information for the strength of respective monitored signals and other may be displayed alone or in a combination with the alerts. The signal strength information could be depicted by, for example, by sequential display segments such as, for example, more than one series of different sized light-emitting diodes (LEDs) that would advantageously enable simultaneous display of at least two different network signal strengths for viewing by the caregiver.

As with the display of externally generated information indicative of alarm conditions, it is possible for alerts for internally generated information indicative of an alarm condition by the relay module 30a to also be displayed by display 36. For example, alerts representative of information during start-up or current status of the relay module 30a and/or current communication or connection status with the WLAN or WPAN 16 and WWAN may be shown on the display elements 36. In another embodiment, the processor 34 may cause the display 36 to include information associated with the charge level of a battery (not shown) contained within the relay module 30a, whether by remaining minutes and/or hours of life or other graphical depictions.

Relay module 30a may preferably be provided as a small physical enclosure (not shown) optionally provided with an integral power plug and power supply circuit, such that the relay module 30a may be directly plugged into and supported by a conventional wall outlet providing commercial AC power.

Figure 4:
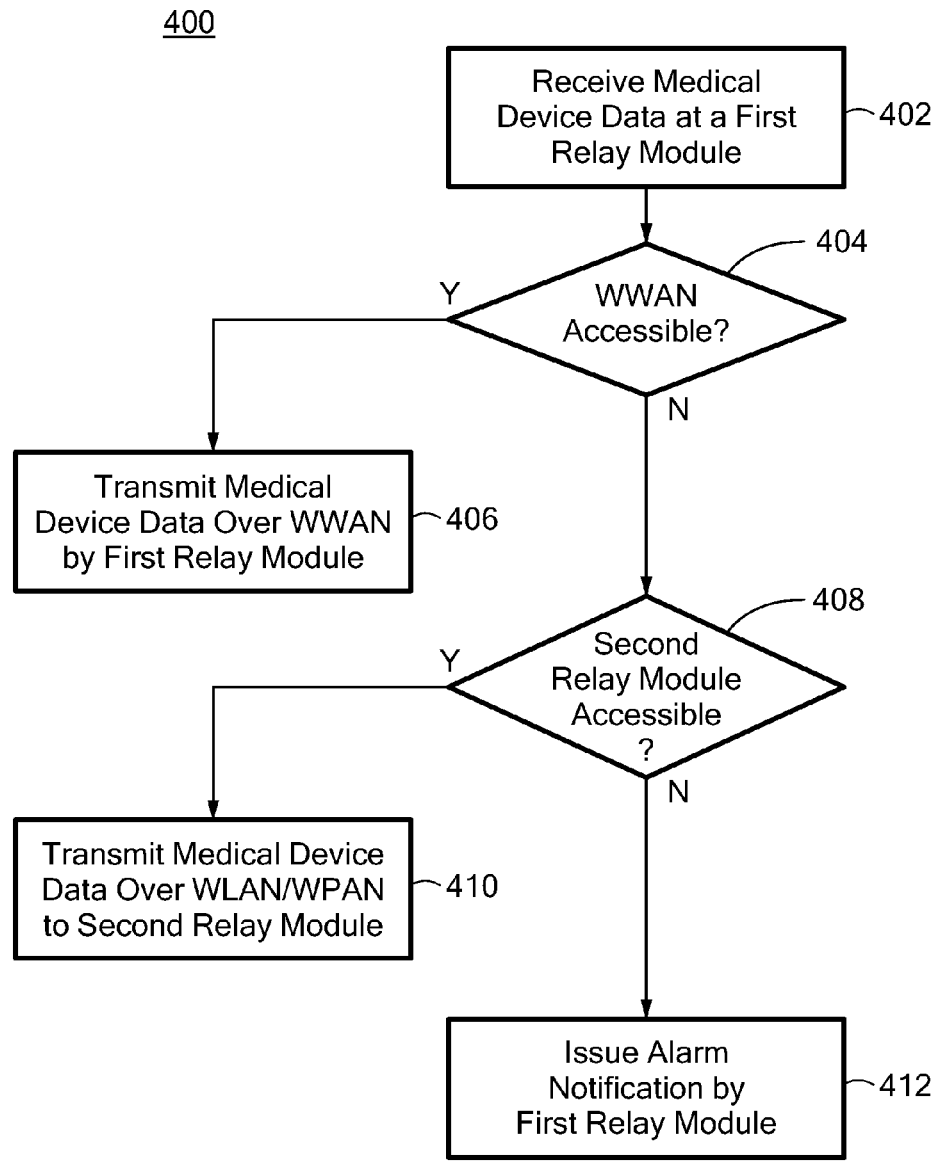
FIG. 4 presents a flow diagram illustrating a first exemplary method of operation for the architecture according to the present invention.

FIG. 4 presents a flow diagram 400 illustrating an exemplary method of operation for the architecture according to FIG. 1(a) and relay module 30, 30a components of FIGS. 2 and 3 relating to the transmission of medical device data obtained from a medical device 10 to the access point 40. At step 402 of the method 400, the medical device data is received at a first one of the relay modules 30a from one of the interface circuits 15 and/or other relay modules 30, 30a over the WLAN or WPAN network 16. At step 404, the processor 34 of the one relay module 30a determines whether the WWAN is accessible by that relay module 30a.

The determination of step 404 may be carried out in a variety of manners. For example, the processor 34 may interrogate the status module 32b of the transceiver 32 at the time of the receipt of the medical device data to determine a status of access for the transceiver 32 to the WWAN (for example, as the result of the transceiver 32 detecting an access signal of the WWAN having adequate signal strength). Alternatively, the processor 34 may interrogate the status module 32b at a different time including, for example, at system start-up, intermittently and/or periodically (for example, hourly), and maintain a status indicator such as in the buffer 35a or the memory 35b to be retrieved at the time of receipt of the medical data. As yet another alternative, the relay module 30, 30a may be assigned a predetermined, fixed role within the network 16. For example, relay modules 30a in the network 16 may be assigned a data routing assignments by a controller or "master" relay module. By definition, the WWAN status for relay module 30 that does not possess WWAN access capability shall have a fixed status of "WWAN inaccessible."

If, as provided for in step 404, the status module 32b indicates that the WWAN is accessible by the transceiver 32, then the processor 34 will proceed to step 406 to instruct the data processing circuit 33 of the one relay module 30, 30a to retrieve the medical device data from the buffer 35a (as necessary) and forward the medical device data to the transceiver 32 for transmission to the access point 40 over the WWAN.

Alternatively, in step 404, the status module 32b may indicate that the WWAN is not accessible by the transceiver 32. For example, if the one relay module 30a is located on a basement floor of the building in an area that is substantially shielded with respect to WWAN signals, the WWAN may not be accessible to the one relay module 30a. In this event, at step 408, the processor 34 determines whether a second relay module 30a is accessible via the WLAN or WPAN 16. Again, this determination may be made in a variety of manners including by instructing the transceiver 31 to send a handshake signal transmission directed to a second relay module 30a and to listen for a reply, or by retrieving a stored status indicator for example via the status module 31b for the second relay module 30a.

If the second relay module 30a is accessible, then the processor 34 instructs the data processing circuit 33 of the one relay module 30a to retrieve the medical device data from the buffer 35a (as necessary) and forward the medical device data to the transceiver 31 for transmission to the second relay module 30a over the WLAN or WPAN 16 at step 410. Alternatively, if the second relay module 30a is inaccessible in step 408, this portion of the process 400 may preferably be repeated to search for a further relay module 30a that is accessible. In the event that no other relay module 30a is available, the processor 34 of the one relay module 30a may preferably issue an alarm notification at step 412. Such an alarm notification may, for example, include one or more local visual and audio alerts as directed by processor 34 via the display 36 or speaker 37, alarm messages directed by the processor 34 to another accessible WLAN or WPAN 16 or WWAN via one or more of the transceivers 31, 32, and/or alarm messages generated by the inbound web server 41 of the access point 40 of FIG. 1(a) after a specified time period (for example, 5 minutes) has been exceeded during which a handshake signal of the relay module 30a is due to be received at the inbound web server 41. The processor 34 may also issue alarm notifications upon failing to receive a handshale signal from other medical devices 10 and/or relay modules 30,30a.

Figure 5A:
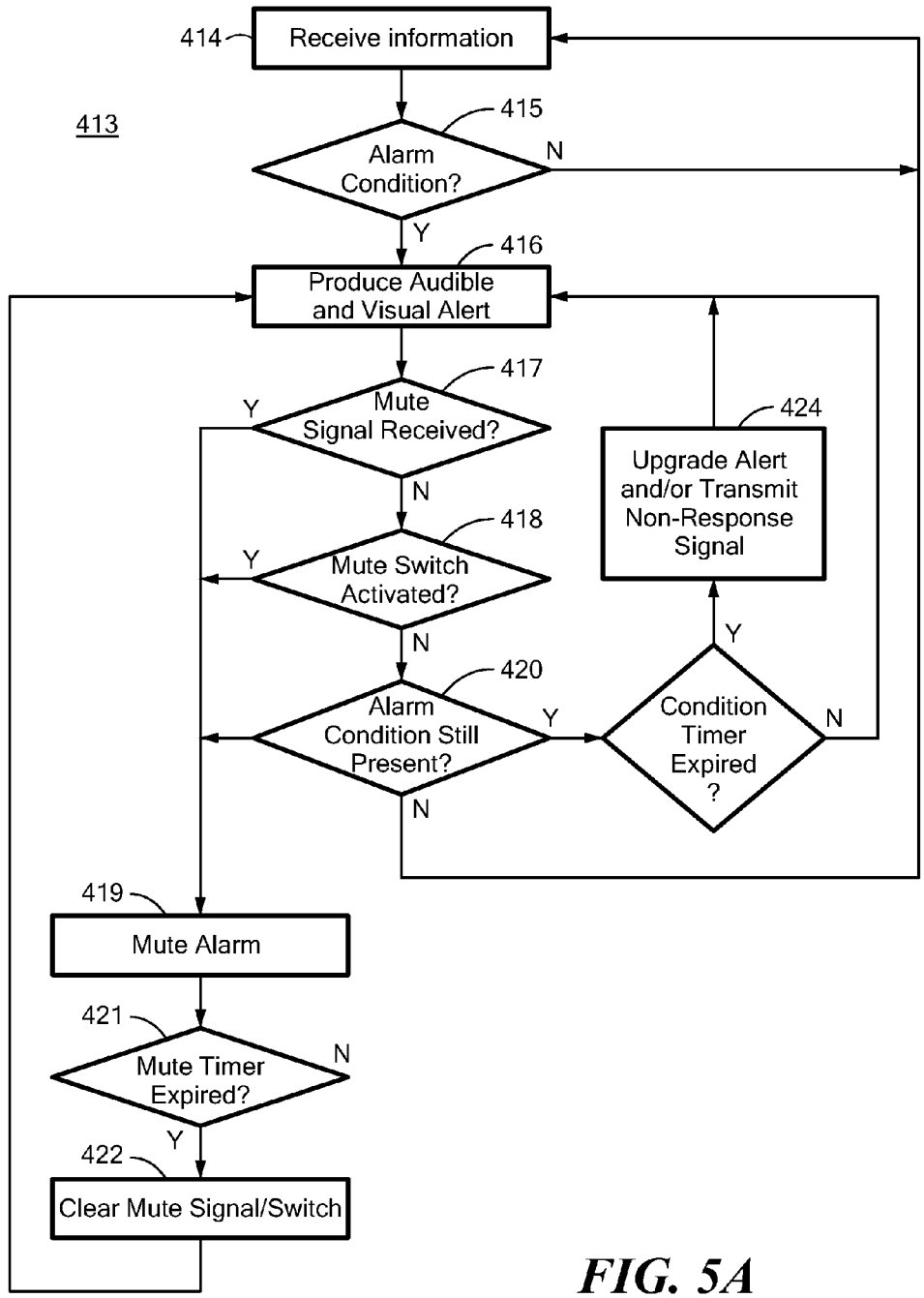
FIG. 5(a) presents a flow diagram illustrating an exemplary alarm and display process.

FIG. 5(a) depicts a flow diagram 413 representing an exemplary alarm alert and display process. In accordance with the flow diagram 413, at step 414 the processor 34 of the relay module 30a of FIG. 3 receives information such as medical device data from a medical device, another relay module or internally generated by the relay module. Then, the method 413, in step 415, determines whether the information obtained in step 414 is indicative of an alarm condition or an alarm condition is otherwise present. If no alarm condition is detected at step 415, then method 413 reverts back to step 414. If, in step 415, an alarm condition is detected based on the obtained information by step 414, the method 413 proceeds to step 416.

In step 416, the processor 34 produces an audible and visual alarm alert by transmitting signals representing an alert to be displayed to the display 36 and/or transmits signals representing speech or other audible information (for an audible alarm) to the speaker 37 of FIG. 3. Alternatively and/or in addition, the processor 34 may transmit the alarm alert to a medical device 10 via the transceiver 31, and/or to the access point 40 via the transceiver 32. Then, the method 413 proceeds to step 417.

In step 417, it is determined whether the module 30a receives medical device data or other information instructing the module to mute or disable the audible alarm or an input signal is otherwise received requesting to mute the sound or disable the audible alarm. If such input signal is received then, in step 419, the processor 34 mutes the speaker 37 to disable the audible alarm. However, in step 417, if no such input signal is received then the method 413 proceeds to step 418.

In step 418, the processor 34 determines whether a user-actuatable switch associated with the input/output circuit 38, e.g., a mute switch of the relay module 30a, has been activated. If such a switch has been activated then the method 413 proceeds to step 419 and the speaker 37 is muted to disable the emitted audible alarm. The method 413 then proceeds at step 421 to determine whether a mute timer has expired after a predetermined time interval (for example, 5 minutes). If so the mute signal is cleared and/or the mute switch is released, and the method 413 returns to step 416 to produce each of the audible and visual alerts.

If in step 418, it is determined that the mute switch has not been activated, then the method 413 proceeds to step 420 where the processor again determines whether the alarm condition is still present based upon, for example, newly received medical device data. If the alarm condition is no longer present, the method 413 proceeds to step 414 and the alarm is disabled. However, if in step 420 the alarm condition is still present, the method proceeds at step 423 to check a condition timer to determine whether the alarm condition has been present for a particular period of time (either fixed in duration for example of five minutes, or for a variable duration based upon the particular alarm condition). If the condition timer has expired in step 423, then in step 424 the emitted audible alarm may advantageously be changed or upgraded in decibel level, pitch, type of sound, duty cycle or speech command to draw greater attention and response to the alarm condition by potential responders, and reapplied at step 416. In addition to, or in the alternative, the relay module 30, 30a at step 424 may transmit a signal to other nearby or remote relay module(s) to alert other potential responders of the alarm condition.

It should be understood that the method of flow diagram 413 may operate with information received from a plurality of medical devices or other wireless relay modules, and may provide the intermittent displaying of respective alarm alerts for particular time intervals or employ different foreground or background colors based upon the type or severity of the alarm condition.

Figure 5B:
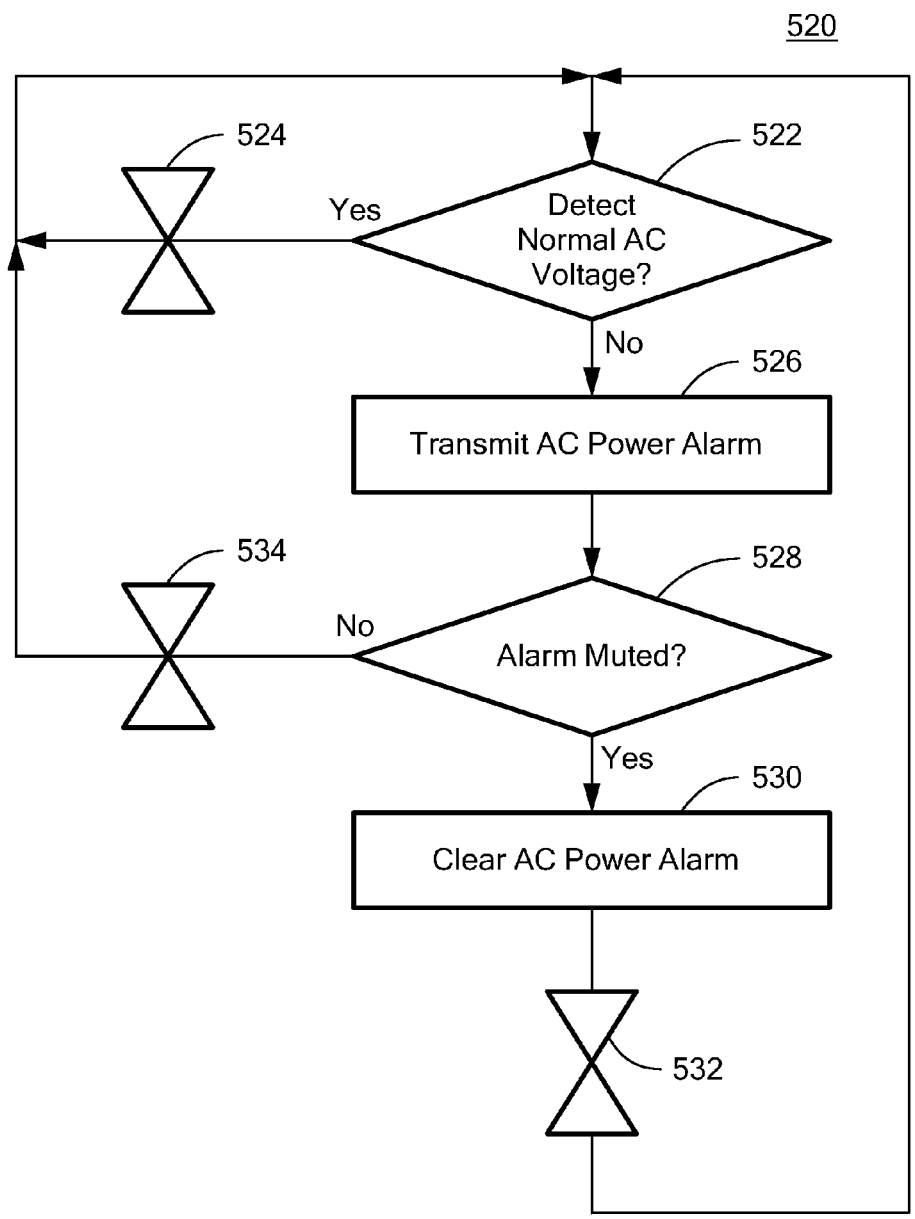
FIG. 5(b) presents a flow diagram illustrating an exemplary alarm process associated with a power characteristic of a wireless relay module in an exemplary architecture according to the present invention.

FIG. 5(b) depicts a flow diagram 520 representing an exemplary alarm monitoring process executed by the processor 34 and the power monitoring device 39b with respect to the AC power supply to the relay module 30a. At step 522, the processor 34 interrogates the power monitoring device 39b to determine whether the external AC power supply is providing a "normal" voltage (for example, 120 VAC, 60 Hz). If the external AC power supply is providing a normal voltage, the processor engages a timer 524 to operate for a predetermined period of time (for example, 2 minutes) and then returns to step 522. If the external AC power supply is not providing a normal voltage (for example, a voltage less than 105 VAC, including 0 VAC resulting from an external AC power disconnect), the processor 34 causes a power alarm message to be transmitted at step 526. At step 528, the processor determines whether an audible portion of the alarm resulting from the transmitted alarm message has been muted (for example, by activating the mute switch of the relay module 30*a*). If yes, the processor 34 transmits a message to clear the alarm at step 530, engages a timer to operate for a second predetermined period (for example, 5 minutes), and then returns to step 522. If not, the processor 34 engages a timer 534 to operate for another predetermined time period (for example, 3 minutes), and then returns to step 522. Alternatively, at step 528, the processor 34 may clear the muted condition rather than clearing the alarm, and release the alarm only if a normal voltage is detected as step 522.

Figure 5C:
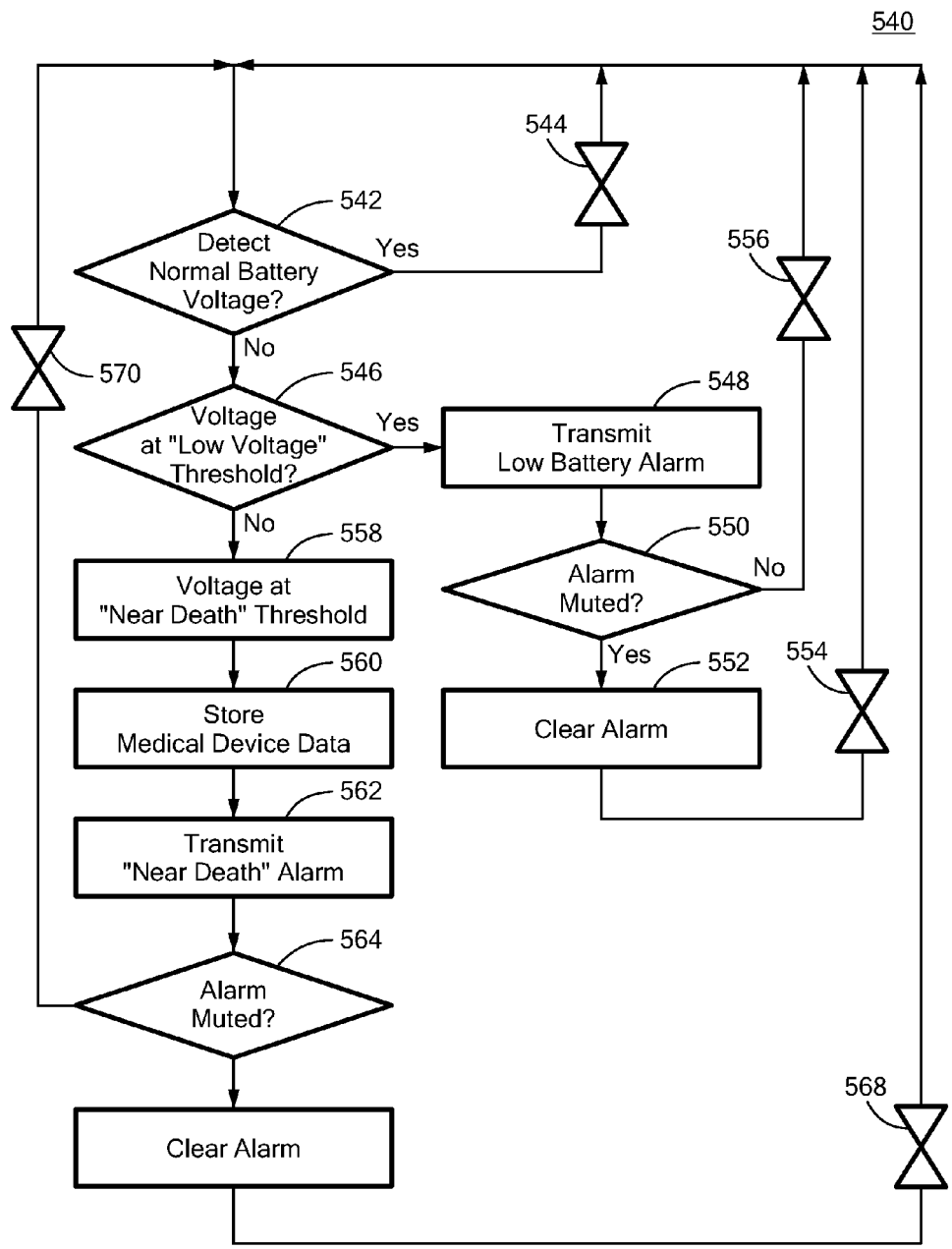
FIG. 5(c) presents a flow diagram illustrating an exemplary alarm process associated with another power characteristic of a wireless relay module in an exemplary architecture according to the present invention.

FIG. 5(*c*) depicts a flow diagram 540 representing an exemplary alarm monitoring process executed by the processor 34 and the power monitoring device 39*b* with respect to the secondary power source 39*c* to the relay module 30*a*. At step 542, the processor 34 interrogates the power monitoring device 39*b* to determine whether the secondary power source 39*c* is providing a "normal" voltage (for example, 9 VDC). If the secondary power source 39*c* is providing a normal voltage, the processor engages a timer 544 to operate for a predetermined period of time (for example, 1 minute) and then returns to step 542.

If the secondary power source 39*c* is not providing a normal voltage (for example, a voltage less than 8.5 VDC), the processor 34 interrogates the power monitoring device 39*b* to at step 546 to determine whether the secondary power source 39*c* is providing a "low" voltage (for example, between 7 and 8.5 VDC). If yes, the processor causes a low battery alarm message to be transmitted at step 548. At step 550, the processor determines whether an audible portion of the alarm resulting from the transmitted alarm message has been muted (for example, by activating the mute switch of the relay module 30*a*). If yes, the processor 34 transmits a message to clear the alarm at step 552, and engages a timer 554 to operate for a predetermined period (for example, 1 minute) and returns to step 542. If not, the processor 34 engages another timer 556 to operate for another predetermined time period (for example, 2 minutes) and then returns to step 542.

If the processor 34 at step 546 determines that the secondary power source 39*c* is not providing a "low" voltage (for example, between 7 and 8.5 VDC), the processor 34 concludes at step 558 that the voltage is a "near death" voltage (for example, less than 7 VDC). The processor 34 then begins at step 560 to store medical device data arriving from one or more medical devices 10 via the wireless relay network and/or from the access point 40 via the internet-accessible wireless communications network in the memory 35*b*, and causes a near death battery alarm message to be transmitted at step 562. At step 564, the processor determines whether an audible portion of an alarm resulting from the transmitted alarm message has been muted (for example, by activating the mute switch of the relay module 30*a*). If yes, the processor 34 transmits a message to clear the alarm at step 566, and engages a timer 568 to operate for a predetermined period (for example, 1 minute) and returns to step 542. If not, the processor 34 engages another timer 570 to operate for another predetermined time period (for example, 2 minutes) and then returns to step 542. If normal battery voltage is detected at step 542, the processor 34 retrieves any medical device data that was stored in the memory 35*b* during the period when a "near death" voltage was detected, and transmits the retrieved medical device data to intended destinations via one or more of the wireless relay network and/or the internet-accessible wireless communications network.

Figure 6:
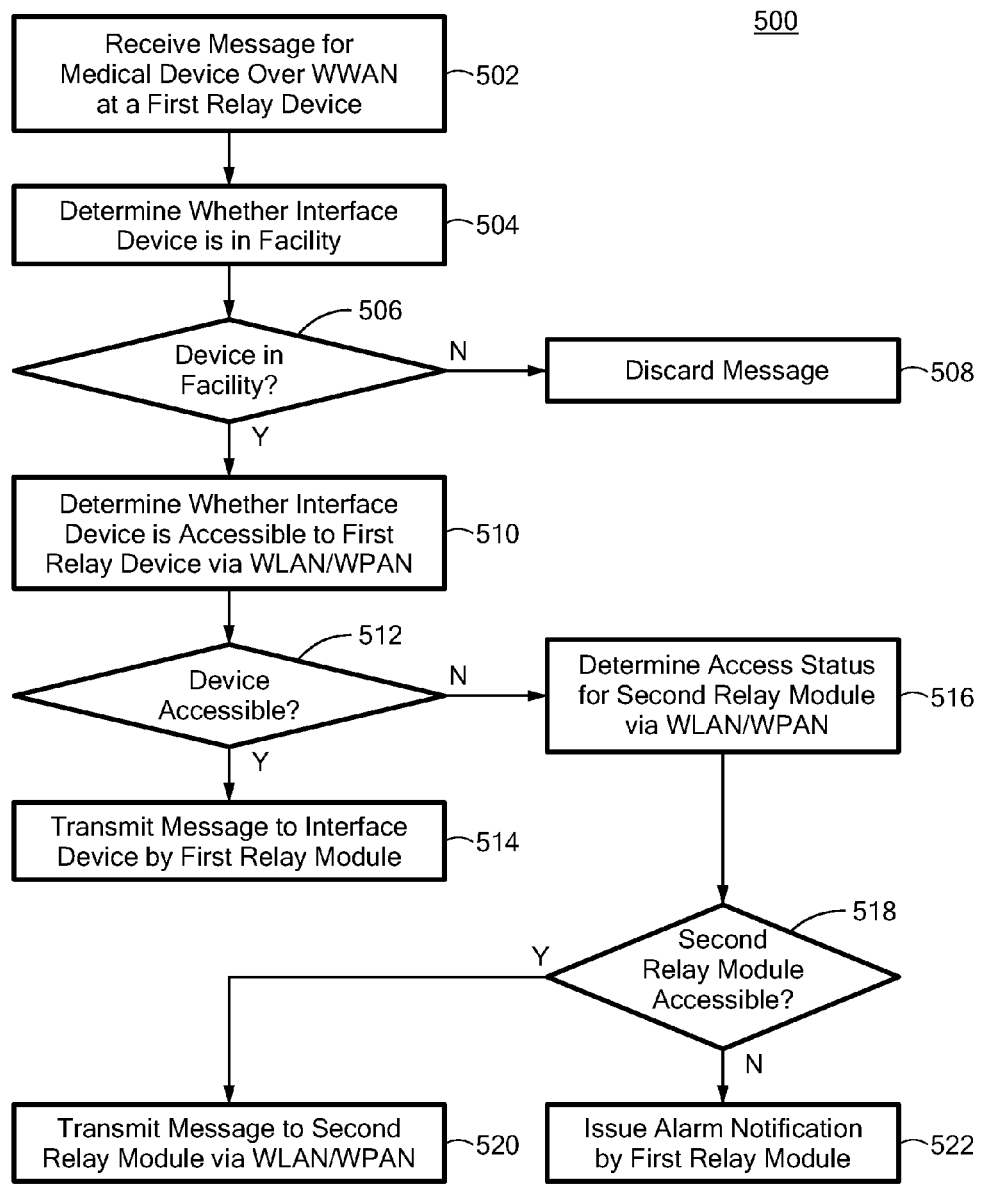
FIG. 6 presents a flow diagram illustrating a second exemplary method of operation for the architecture according to the present invention.

FIG. 6 presents a flow diagram illustrating another exemplary method of operation 500 for the architecture according to FIG. 1(*a*), relating to the transmission of a message from the access point 40 to be received by one of the medical devices 10. This enables the access point 40, for example, to communicate with medical devices in order to download new firmware or software, to respond to error messages initiated by the medical devices (for example, to re-set a device or remove it from service, or to run device diagnostics), and to operate the medical device (for example, to adjust a set point of the medical device, such as a flow rate on a feeding pump).

At step 502 of the method 500, the message is received at the first one of the relay modules 30*a* from the access point 40 via the WWAN. At step 504, the one relay module 30 determines whether the message is intended to reach one of the interface circuits 15 and/or other relay modules 30, 30*a* located in the facility 20. This may be accomplished, for example, by maintaining a list of active devices 15 and modules 30, 30*a* in the buffer 35*a* or in a manner otherwise accessible to the one relay module 30*a*, or coding an identifier of the interface circuit 15 or module 30, 30*a* to include an identity of the facility 20 that is stored in the buffer 35*a* or is otherwise identifiable to the one relay module 30. In the alternative, the received message may include a device identifier such as a serial number or an assigned identifier. Such a received message would then be broadcasted to all or a subset of interface circuits 15 in the facility and each interface circuit 15 determines if it was the intended recipient or should otherwise act upon or ignore the message.

If the one relay module 30*a* determines at step 506 that the interface circuit 15 or module 30, 30*a* is not located in the facility, the one relay module 30 may preferably proceed to discard the message at step 508, and/or alternatively alert by responding to the access point 40 with a non-delivery message. If the interface circuit 15 is located in the facility 20, the one relay modular 30 determines at step 510 whether the interface circuit 15 or relay module 30, 30*a* is accessible to the one relay device 30 via the WLAN or WPAN (for example, by consulting a list stored in the buffer 35*a* or that is otherwise accessible to the one relay module 30, or by instructing the transceiver 31 to send a handshake or test transmission directed to the interface circuit 15 and to listen for a reply).

If the one relay module 30*a* determines at step 512 that the device 15 or relay module 30, 30*a* is accessible, then at step 514, it transmits the message via network 16 to that device or relay module via the transceiver 31. If the one relay module 30*a* alternatively determines at step 512 that the device or relay module is not accessible, it proceeds at step 516 to determine whether a second relay module 30, 30*a* is accessible via the WLAN or WPAN (for example, by instructing the transceiver 31 to send a handshake or test transmission directed to the second relay module and to listen for a reply). If the second relay module 30, 30*a* is available, then the one relay module 30 forwards the message to the transceiver 31 for transmission to the second relay module 30, 30*a* over the WLAN or WPAN. If the second relay module 30, 30*a* is inaccessible, then this portion of the process 500 may preferably be repeated to search for a third relay module 30, 30*a* that is accessible. Alternatively, or in the event that no other relay module 30, 30*a* is available, the one relay module 30 may preferably issue an alarm notification at step 522, preferably in one of the same manners described above in reference to the method 400 of FIG. 4.

Figure 7:
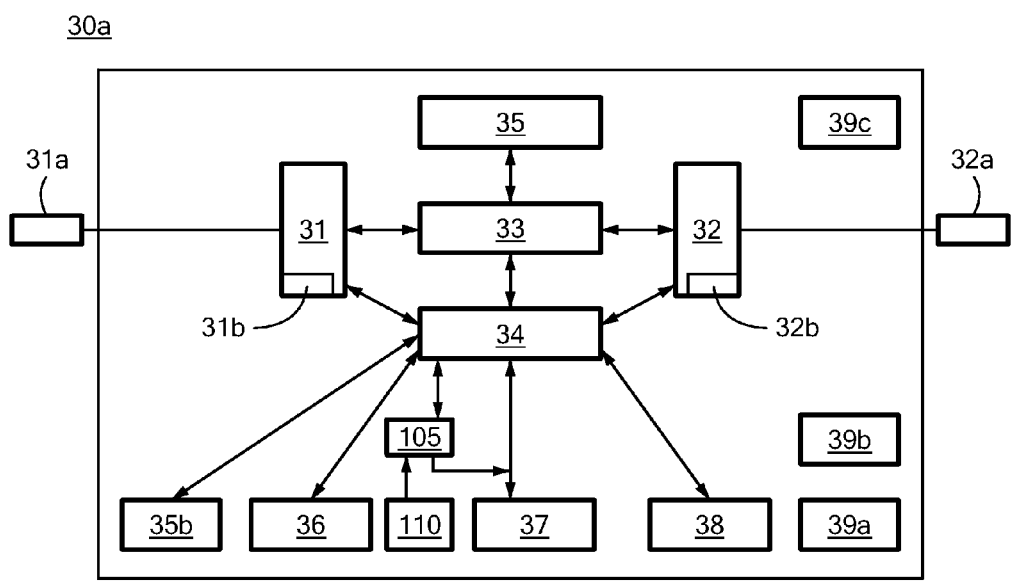
FIG. 7 presents a schematic diagram illustrating a further exemplary embodiment of a wireless relay module with voice interaction capabilities.

FIG. 7 depicts a block diagram of an exemplary alternative embodiment of the relay module 30a of FIG. 3 that enables voice communication and interaction between a caregiver proximate the relay module 30a and a clinician or technician at the remote monitoring device. The identical components in the FIGS. 3 and 7 are like numbered including, for example, the first and second transceivers 31 and 32, data processing circuit 33, processor 34 and data buffer 35a. The relay module 30a of FIG. 7 further includes a speech codec 105 connected to a microphone 110 and the speaker 37.

The particular speech codec selected for the codec 105 is not critical to the present invention as long as it is compatible and/or interoperable with the speech codec of the corresponding remote monitoring device. Suitable codecs for the speech codec 105 include, for example, fixed rate codecs such as voice-over-Internet-protocol (VoIP) codecs in compliance with the ITU standard H.323 recommended protocol. Speech coding standards in accordance with VoIP include ITU standards G.711 (PCM), G.723.1 (MP-MLQ & ACELP), G.729 (CSACELP), GSM-FR; or Adaptible Multi-Rate (AMR) standards such the European Telecommunication Standard Institute (ETSI) and Third Generation Partnership Project (3GPP) IMT-2000. Alternatively, it is possible to employ codecs useable for transmitting encoded speech signals over a mobile telephone network.

The configuration of the relay module 30a of FIG. 7 enables a patient or caregiver proximate the relay module 30a to engage in a conversation with a user (for example, a clinician or technician) proximate the remote monitoring device using, for example, a VoIP or VoIP-like exchange of encoded speech signals. Specifically, in operation of the relay module 30a of FIG. 7, speech uttered by the caregiver proximate the relay module 30a is converted by microphone 110 to analog speech signals that are digitized and encoded by the codec 105. The processor 34 then transmits the corresponding digitized and encoded speech signals produced by the codec 105 directly over the wireless internet-accessible network alone or in combination with the wireless relay module network to the remote monitoring device. The remote monitoring device then decodes the digitized and encoded speech signals and converts such decoded signals into analog signals supplied to a speaker to generate the speech sounds heard by the clinician or technician.

Conversely, digitized and encoded speech signals representing speech of the clinician or technician transmitted by the remote monitoring device are received by the module 30a wherein the processor 34 supplies such signals to the codec 105 which decodes the signals and converts the decoded signals to analog signals that are supplied to the speaker 37.

Although the implementation of the codec 105 and microphone 110 has been described with regard to exchanging VoIP signals, it should be readily understood that any method of communicating speech signals may be employed for carrying out the invention including, for example, utilizing a cellular or mobile telephone codec or modem for codec 105 to transmit and receive speech signals, e.g., CDMA- or GSM-compliant speech signals over a mobile telephone network. Further, it is possible according to the invention for the codec 105 to be implemented as hardware and/or software in a single chip, chip set or as part of the processor 34.

In an alternative embodiment, it is possible to implement speech detection and/or recognition functionality into the codec 105 or processor 34 to enable the relay module 30a to identify specific command words to initiate the carrying out of a corresponding responsive/interactive action. For example, such speech recognition functionality may be triggered by processing signals supplied by the microphone 110 to identify terms "Help", "Emergency" or "Call 911." Upon detecting such trigger terms, the processor 34 initiates the process of dialing an emergency response service such as "911," with or without using synthesized or recorded speech to request confirmation from the caregiver to place such a call and initiate communication between the caregiver and the emergency response service. The dialing may be performed by hardware or software implemented in the processor 34, codec 105 or other components coupled to the processor 34. The speech recognition functionality may alternatively or additionally transmit a text message or other text or audio-visual correspondence to the emergency response service based upon identified spoken works or commands by the caregiver.

It should be readily understood that the relay module 30a of FIG. 7 is shown with the codec 105 and microphone 110 in combination with the display 37 for illustration purposes only. It is possible in accordance with the invention to implement a relay module with the codec without a display or a relay module with a display and not a codec (as depicted in FIG. 3).

Figure 8:
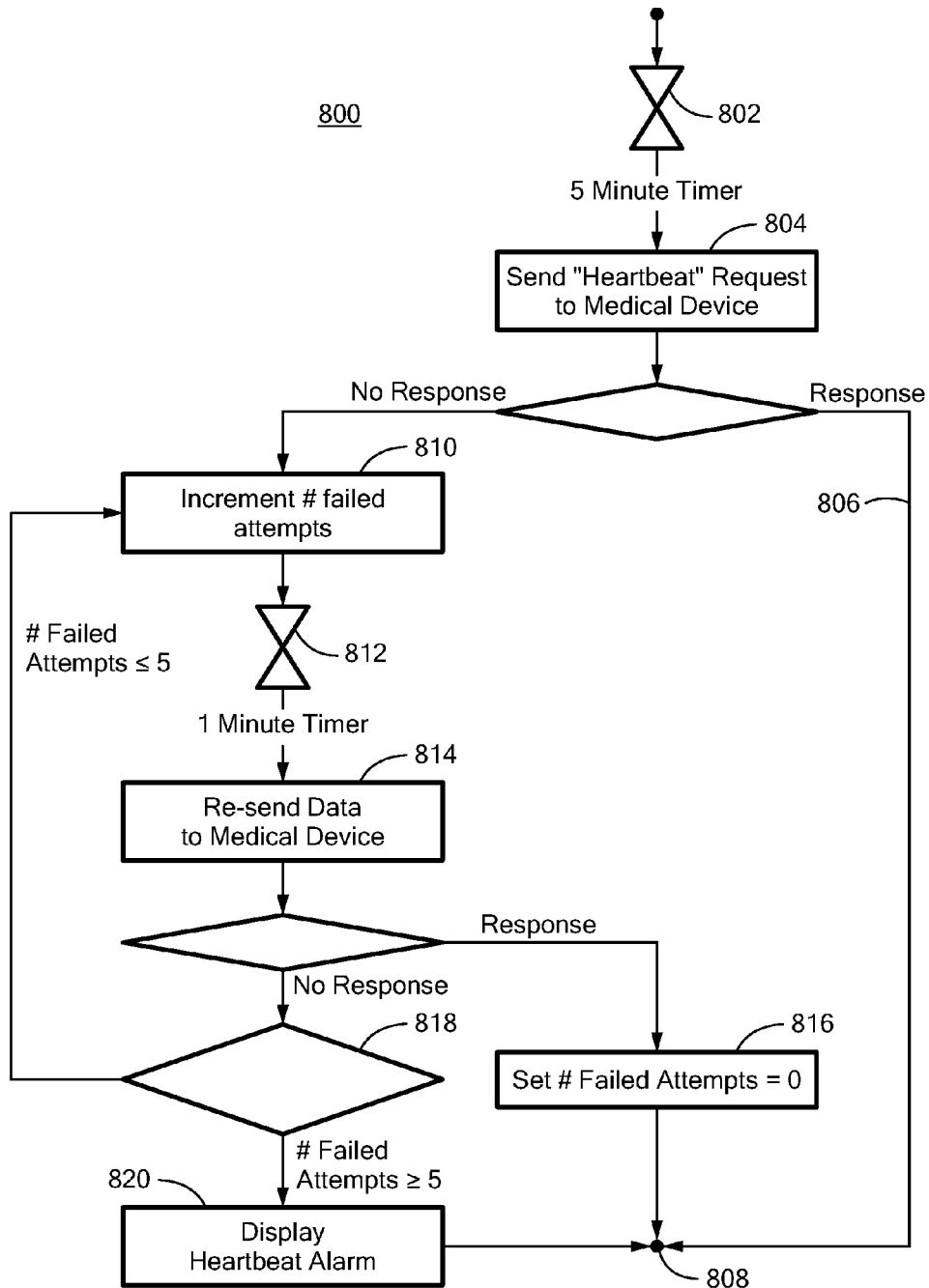
FIG. 8 presents a flow diagram illustrating another exemplary alarm process of a wireless relay module according to the present invention.

FIG. 8 depicts a flow diagram 800 representing an exemplary process executed by the wireless relay module to determine whether communications with a particular medical device 10 can be carried out over the wireless relay network 16. The process begins with the processor 34 of the wireless relay module 30a engaging a timer 802 for a predetermined period of time (for example, 5 minutes). After expiration of the timer 802, the processor 34 instructs the transceiver 31 to transmit a "heartbeat" request to the medical device 10 over the wireless relay network. If a response is received by the transceiver 31 to the request, the process concludes at step 808 and the processor once again engages the timer 802.

If no response to the request is received by the transceiver 31, the processor 34 increments a request counter at step 810 and engages another timer 812 for another predetermined period of time (for example, 1 minute). Then, the processor 34 proceeds to resend the heartbeat request at step 814. If a response is received by the transceiver 31 to the resent request, the process concludes at step 808 and the processor again engages the timer 802. If no appropriate response is received, the processor 34 proceeds at step 818 to determine whether the request counter exceeds a predetermined value (for example, 5). If this value is exceeded, the processor 34 causes at step 820, a heartbeat alarm to be displayed by the display 36 and/or be audibly signaled by the speaker 37, and/or transmits a message via at least one of the transceivers 31, 32 to the access point 40 and/or to another internet-accessible and/or wireless network-accessible recipient. The process then continues at step 808 and the processor once again engages the timer 802. If the predetermined value of the request counter is not exceeded at step 818, the process returns to step 810.

One of skill in the art will readily understand that, in addition to requesting a "heartbeat" from the medical device 10 according to the process 800 of FIG. 8, a variety of other measures may be obtained to determine whether communications with a particular medical device 10 can be carried out over the wireless relay network 16. For example, the processor 34 of the wireless relay module 30a may alternatively instruct the status module 31b associated with the transceiver 31 to determine one of a variety of measures of signal quality for the wireless relay network signals being received from a medical device 10 (for example, including a signal strength or data rate of the transmitted signal).

Alternatively or in addition, the processor 34 may instruct the location device 39a to obtain location information of the wireless relay module, and compare this to location information obtained from the medical device and/or by other means (for example, by using a conventional triangulation algorithm measuring transit times of signals transmitted by the medical device 10 to several wireless relay modules 30a with known locations) in order to determine whether the medical device 10 (for example, in the possession of an ambulatory patient) has moved outside of an area for safe communications with the relay module 30a (i.e., is outside the "geo-fence").

In this case, the processor 34 may preferably transmit a "lost device" alarm message via at least one of the transceivers 31, 32 to the access point 40 and/or to any other Internet-accessible and/or wireless network-accessible recipients. In addition, in order to conserve power and or bandwidth of the wireless relay module 30a, the processor 34 may suspend all other measurements made to determine communications health with the medical device 10 (for example, heartbeat requests and signal quality measurements) until it has been determined that the medical device 10 is back within the geo-fence.

One of skill in the art will also readily understand that the elements used by the wireless relay module 30a to determine whether communications with a particular medical device 10 can be carried our over the wireless relay network may be replicated in the medical device 10, such that the medical device 10 may determine whether communications with a particular wireless relay module 301 can be carried out over the wireless relay network, and to issue a visual and/or audible alarm at the medical device 10 when communications with the wireless relay module 30a cannot be carried out. This feature would be particularly useful, for example, to a patient in an ambulatory setting as a means for learning that he/she has exited the geo-fence.

The architecture disclosed herein for providing networked communications between a series of medical devices and a remote monitoring device provides a number of distinct advantages in comparison to other monitoring systems. By employing ZIGBEE mesh networks based on the IEEE 802.15.4 standard according to a preferred embodiment for wireless communications between the medical devices 10 and relay modules 30, 30a, power and size requirements can be minimized so that the interface circuits 15 can be easily and inexpensively applied to and/or integrated with the medical devices 10.

By introducing relay modules 30a that are part of the ZIGBEE mesh network with the capacity to directly access off-site monitoring devices via a WWAN, access to and reliance on existing and potentially unreliable LAN facilities at a facility can be avoided. By incorporating relay features into the relay modules 30a that relay communications from a first relay module 30a through a second relay module 30a in the event that WWAN access to the first relay module 30a has been compromised, the present invention improves reliability and enables the use of conventional, low-cost cellular transceivers in the relay modules 30a for accessing the WWAN.

By limiting the configuration of cellular transceivers to just the relay modules 30a, costs can be further reduced. In addition, providing the relay modules 30a in a compact enclosure facilitates the relay modules 30a to be easily connected to reliable commercial power sources and easily moved when needed to reconfigure the ZIGBEE mesh networks according to facilities changes.

It should of course be understood that while the present invention has been described with respect to disclosed embodiments, numerous variations are possible without departing from the spirit and scope of the present invention as defined in the claims. For example, the present invention may be based on any of a number of current and future WPAN, WLAN and WWAN standards beyond those explicitly described herein. It should also be understood that it is possible to use exclusively relay modules 30a in the WLAN or WPAN network 16 of FIGS. 1 and 2, with transceivers for communicating with other relay modules as well as over the WWAN.

In addition, respective interface circuits useable with the present invention may include components of and perform the functions of the module 30 to provide greater flexibility in accordance with the present invention. Further, numerous configurations of components for relay module 30a are useable with the present invention beyond the components shown in FIGS. 3 and 7. For instance, an input-output buffer may be used with respective switches under control of a processor for directing medical device data to transceivers 31, 32 as needed. Moreover, it is intended that the scope of the present invention include all other foreseeable equivalents to the elements and structures as described herein and with reference to the drawing figures.

We claim:
1. A wireless relay module comprising:
an electrical connector configured to receive primary power from a power source;
a battery configured to provide secondary power upon a changed characteristic of primary power;
a first receiver capable of wirelessly receiving medical device data over a wireless relay network from at least one medical device;
a first transmitter capable of wirelessly transmitting medical device data over the wireless relay network;
a second transmitter capable of wirelessly transmitting medical device data over an Internet-accessible wireless communications network;
a processor coupled to the first and second transmitters, said processor capable of controlling said wireless relay module to select one of said first or second transmitter for transmitting medical device data received by said first receiver; and
said processor further capable of producing a power alarm signal upon the changed characteristic of the primary power, determining whether at least a second wireless relay module communicating on the same wireless relay network is accessible to receive a message, and sending the power alarm signal to at least the second wireless relay module for proliferation of the power alarm signal over the network if it is determined that the second wireless relay module is accessible.

2. The wireless relay module of claim 1, further comprising at least one of a visual display or speaker coupled to the processor and configured to provide a visual and/or audio alert.

3. The wireless relay module of claim 1, wherein the second transmitter is configured to transmit an alert signal to a remote monitoring device over the internet-accessible wireless communications network.

4. The wireless relay module of claim 1, wherein the processor is capable of transmitting an alarm signal when a charge state of the battery falls below a particular charge level.

5. The wireless relay module of claim 4, wherein the processor is configured to modulate the alarm signal to be indicative of the state of charge of the battery between a low charge state and a zero charge state.

6. The wireless relay module of claim 1 further comprising a sensor capable of detecting disconnection of the connector from the power source.

7. The wireless relay module of claim 6, wherein the processor is capable of transmitting an alarm signal when the sensor detects disconnection of the connector from the power source.

8. The wireless relay module of claim 1 further comprising: a memory electrically connected to said controller, said memory capable of storing said received medical device data.

9. The wireless relay module of claim 8 wherein at least one of the first or second transmitters is configured to transmit the stored medical device data upon restoration of the primary power.

10. The wireless relay module of claim 1 wherein said first transmitter is configured to, upon generation of the alarm signal, send a notice to the medical device or to another wireless relay module indicating that the primary power has been disrupted.

11. The wireless relay module of claim 10 wherein said first transmitter is further configured to, upon restoration of the primary power, send a notice to the medical device or to the other wireless relay module indicating that the primary power has been restored.

12. The wireless relay module of claim 1 wherein said processor is capable of transmitting to the remote monitoring device at least one of the medical data or an acknowledgement signal in response to receipt of a particular signal transmitted by the remote monitoring device.

13. The wireless relay module of claim 1 wherein the wireless relay network is a mesh network and the processor includes a network interface for communicating over the mesh network.

14. The wireless relay module of claim 1 wherein the processor is configured to store the device data in a memory prior to loss of power when a voltage level is below a near-death voltage.

15. The wireless relay module of claim 1 wherein the wireless relay is capable of producing an alarm in response to loss of AC power and is capable of producing an alarm in response to a low battery voltage level.

16. The wireless relay module of claim 1 wherein the processor is further configured to determine if an audible portion of the alarm has been muted and, if so, to transmit a message to clear the alarm.

17. A wireless relay module comprising: an electrical connector configured to receive power from a power source;
a first receiver capable of wirelessly receiving medical device data over a wireless relay network from at least one medical device;
a first transmitter capable of wirelessly transmitting medical device data over the wireless relay network;
a second transmitter capable of wirelessly transmitting data over an internet-accessible wireless communications network;
and a processor coupled to the first and second transmitters, said processor capable of controlling said wireless relay module to select one of said first and second transmitter for transmitting the medical device data received by said first receiver; and
said processor further capable of producing a power alarm signal upon a changed characteristic of the received power, determining whether at least a second wireless relay module communicating on the same wireless relay network is accessible to receive a message, and sending the power alarm signal to at least the second wireless relay module for proliferation of the power alarm signal over the network if it is determined that the second wireless relay module is accessible.

18. The wireless relay module of claim 17, further comprising at least one of a visual display or speaker coupled to the processor and configured to provide a visual and/or audio alert.

19. The wireless relay module of claim 17, wherein the second transmitter is configured to transmit an alert signal to a remote monitoring device over the internet-accessible wireless communications network.

20. The wireless relay module of claim 17, wherein said power source is a battery and the processor is capable of transmitting an alarm signal when the charge state of the battery falls to or below a particular charge level.

21. The wireless relay module of claim 20, wherein the processor is configured to modulate the alarm signal to be indicative of the state of charge of the secondary power source between a low charge state and a zero charge state.

22. The wireless relay module of claim 17 further comprising: a memory electrically connected to said controller, said memory capable of storing said received medical device data.

23. The wireless relay module of claim 22 wherein at least one of the first and second transmitters is configured to transmit the stored medical device data based upon the characteristic of received power.

24. The wireless relay module of claim 17 wherein said first transmitter is configured to, upon generation of the alarm signal, send a notice to the medical device or to another wireless relay module.

25. The wireless relay module of claim 17 wherein said processor is capable of transmitting to a remote monitoring device at least one of the medical device data and an acknowledgement signal in response to receipt of a particular signal transmitted by the remote monitoring device.

26. A process for operating a relay module in a medical device wireless network, the relay module comprising a first transmitter in communication with a wireless relay network, comprising:
receiving medical device data from at least one medical devices over the wireless relay network;
transmitting the medical device data to a second relay module through the medical device network or to a web server through and internet-accessible wireless network, based upon an accessibility condition of the wireless relay module to the internet-accessible wireless network; and
upon disruption of primary power to the relay module, connecting the relay module to a secondary power source, determining whether at, least a second wireless relay module communicating on the same wireless network is accessible to receive a message, and sending a power alarm signal to at least the second wireless relay module for proliferation of the power alarm signal over the network if it is determined that the second wireless relay module is accessible.

27. The process of claim 26 further comprising determining the accessibility condition of the internet-accessible wireless communications network from the second transmitter of said relay module.

28. The process of claim 26 further comprising providing a visual and/or audio alert based upon the generated alarm signal.

29. The process of claim 26 further comprising transmitting, via the second transmitter, an alert signal to a remote monitoring device over the internet-accessible wireless communications network after connecting the wireless relay module to the secondary power source.

30. The process of claim 26 further comprising transmitting, via the first transmitter, an alert signal to at least one of another wireless relay module and the medical device based upon the alarm signal.

31. The process of claim 26 further comprising transmitting, via at least one of the first or second transmitters, a second alarm signal when the charge state of the secondary power source falls below a particular charge level.

32. The process of claim 31 wherein the particular charge level indicates one of a low battery condition or a near dead battery condition, and the alarm signals for indicating each of the low battery condition or the near dead battery condition are indicative of its depreciated charge level.

33. The process of claim 26, further comprising storing the received medical device data in a memory of the relay module.

34. The process of claim 32, further comprising transmitting, via at least one of the first or second transmitters, the stored medical device data upon restoration of the primary power.

35. The process of claim 33, further comprising upon restoration of the primary power, sending, via the first transmitter, a notice to the medical device or to another wireless relay module indicating that the primary power has been restored.

36. A wireless relay module comprising:
    a first receiver capable of wirelessly receiving medical device data over a wireless relay network from at least one medical device;
    a first transmitter capable of wirelessly transmitting the medical device data to at least a second wireless relay module over the wireless relay network;
    a second transmitter capable of wirelessly transmitting the medical device data over an internet-accessible wireless communications network;
    an alarm indicator and a processor coupled to the first and second transmitters and the alarm indicator, said processor capable of selecting one of said first and second transmitter for transmitting medical device data received by said first receiver; and
    said processor further capable of activating the alarm indicator if a characteristic of a signal received over the wireless relay network from a medical device falls below a particular threshold, determining, whether at least a second wireless relay module communicating on the same wireless relay network is accessible to receive a message and sending an alarm signal to at least the second wireless relay module to proliferate the alarm signal over the wireless relay network if it is determined that the second wireless relay module is accessible.

37. The wireless relay module of claim 36 wherein said characteristic is signal strength.

38. The wireless relay module of claim 36 wherein said characteristic is data rate.

39. The wireless relay module of claim 36 wherein said characteristic is indicative of distance between said relay module and said medical device.

40. The wireless relay module of claim 36 wherein the second transmitter is capable of transmitting an alert to a remote monitoring device upon interruption of the receipt of the medical device data from the medical device.

41. A process for operating a relay module in a medical device wireless network, the relay module comprising a first transmitter in communication with a wireless relay network, comprising:
    receiving medical data from at least one medical device over the wireless relay network;
    determining the status of an internet-accessible wireless communications network in communication with a said wireless relay module;
    transmitting said medical device data from said at least one medical device over said internet-accessible wireless communications network if said determined status satisfies a particular criteria;
    transmitting said medical device data from said at least one medical device to a second relay module over the wireless relay network if said determined status fails to satisfy the particular criteria;
    monitoring a characteristic of a received signal over the wireless relay network from said at least one medical device;
    generating an alarm if said monitored characteristic is outside of predetermined limits;
    determining whether at least a second wireless relay module communicating on the same wireless relay network is accessible to receive the alarms; and
    sending the alarm to at least a second wireless relay module if it is accessible to receive the alarm to proliferate the alarm over the wireless relay network.

42. The process of claim 41 wherein said characteristic is signal strength.

43. The process of claim 41 wherein said characteristic is data rate.

44. The process of claim 41 wherein said characteristic is indicative of distance between said relay module and said medical device.

45. The process of claim 41 wherein generating the alarm further comprises transmitting a notice regarding the alarm to a remote monitoring device.

* * * * *